United States Patent
Nguyen et al.

(10) Patent No.: US 12,281,134 B2
(45) Date of Patent: *Apr. 22, 2025

(54) ELECTROCHEMICALLY-CLEAVABLE LINKERS

(71) Applicant: MICROSOFT TECHNOLOGY LICENSING, LLC, Redmond, WA (US)

(72) Inventors: Bichlien Nguyen, Seattle, WA (US); Jake Smith, Seattle, WA (US); Karin Strauss, Seattle, WA (US)

(73) Assignee: MICROSOFT TECHNOLOGY LICENSING, LLC, Redmond, WA (US)

( * ) Notice: Subject to any disclaimer, the term of this patent is extended or adjusted under 35 U.S.C. 154(b) by 982 days.

This patent is subject to a terminal disclaimer.

(21) Appl. No.: 16/781,987

(22) Filed: Feb. 4, 2020

(65) Prior Publication Data
US 2021/0238577 A1    Aug. 5, 2021

(51) Int. Cl.
  *C07H 19/10*   (2006.01)
  *C12P 19/34*   (2006.01)
  *C12Q 1/6834*  (2018.01)
  *C12N 9/12*    (2006.01)
  *C12N 9/96*    (2006.01)

(52) U.S. Cl.
  CPC .............. *C07H 19/10* (2013.01); *C12P 19/34* (2013.01); *C12Q 1/6834* (2013.01); *C12N 9/1264* (2013.01); *C12N 9/96* (2013.01); *C12Y 207/07031* (2013.01)

(58) Field of Classification Search
  None
  See application file for complete search history.

(56) References Cited

U.S. PATENT DOCUMENTS

| | | | |
|---|---|---|---|
| 7,494,797 B2 | 2/2009 | Mueller et al. | |
| 10,059,929 B2 | 8/2018 | Efcavitch et al. | |
| 11,591,361 B2* | 2/2023 | Nguyen | C07H 19/10 |
| 2008/0026379 A1* | 1/2008 | Siddiqi | C07H 19/06 |
| | | | 536/25.32 |
| 2009/0093381 A1 | 4/2009 | Wang et al. | |
| 2013/0261014 A1* | 10/2013 | Vorobiev | C12Q 1/6846 |
| | | | 435/6.12 |
| 2020/0384434 A1 | 12/2020 | Nguyen et al. | |
| 2022/0204544 A1* | 6/2022 | Nguyen | C25B 3/05 |

FOREIGN PATENT DOCUMENTS

| | | | |
|---|---|---|---|
| EP | 2669291 A1 | 12/2013 | |
| WO | 2005024018 A1 | 3/2005 | |
| WO | 2009051807 A1 | 4/2009 | |
| WO | 2016182984 A1 | 11/2016 | |
| WO | WO-2017101785 A1 * | 6/2017 | ......... A61K 31/7072 |
| WO | 2017223517 A1 | 12/2017 | |
| WO | 2018102554 A1 | 6/2018 | |
| WO | 2020157439 A1 | 8/2020 | |
| WO | 2021158412 A1 | 8/2021 | |

OTHER PUBLICATIONS

U.S. Appl. No. 18/157,449, filed Jan. 2023, Nguyen, Bichlien Hoang et al., 536/026.8.*
English machine translation of WO2017/101785, downloaded from worldwide.espacenet.com (Year: 2017).*
"International Search Report and Written Opinion Issued in PCT Application No. PCT/US21/015345", Mailed Date: Jul. 13, 2021, 19 Pages. (MS# 407979-WO-PCT).
Palluk, et al., "De novo DNA Synthesis using Polymerasenucleotide Conjugates", In Journal of Nature Biotechnology, vol. 36, Issue 7, Jun. 18, 2018, 11 Pages.
"Invitation to Pay Additional Fees issued in PCT Application No. PCT/US21/015345", Mailed Date: May 19, 2021, 14 pages (MS# 407979-WO-PCT).
"Non Final Office Action Issued in U.S. Appl. No. 17/162,546", Mailed Date: May 2, 2022, 9 Pages. (MS# 409297-US-NP).
Ahn, et al., "ATP-Conjugated Peptide Inhibitors for Calmodulin-Dependent Protein Kinase II", In Journal of Bioorganic & Medicinal Chemistry Letters, vol. 17, Issue 1, Jan. 1, 2007, pp. 147-151.
"International Search Report and Written Opinion Issued in PCT Application No. PCT/US21/062500", Mailed Date: Jun. 28, 2022, 13 Pages. (MS# 409297-WO-PCT).
Wong, et al., "Direct Site-Selective Covalent Protein Immobilization Catalyzed by a Phosphopantetheinyl Transferase", In Journal of the American Chemical Society, vol. 130, Issue 37, Aug. 23, 2008, pp. 12456-12464.
"Notice of Allowance Issued in U.S. Appl. No. 17/162,546", Mailed Date: Oct. 25, 2022, 8 Pages. (MS# 409297-US-NP).
Bi, et al., "Building Addressable Libraries: The Use of "Safety-Catch" Linkers on Microelectrode Arrays", In Journal of the American Chemical Society, Dec. 15, 2010, 9 Pages.

(Continued)

Primary Examiner — Eric Olson
(74) Attorney, Agent, or Firm — Benjamin Keim; Newport IP, LLC

(57) ABSTRACT

This disclosure provides electrochemically-cleavable linkers with cleavage potentials that are less than the redox potential of the solvent in which the linkers are used. In some applications, the solvent may be water or an aqueous buffer solution. The linkers may be used to link a nucleotide to a bound group. The linkers include a cleavable group which may be one of a methoxybenzyl alcohol, an ester, a propargyl thioether, or a trichloroethyl ether. The linkers may be cleaved in solvent by generating an electrode potential that is less than the redox potential of the solvent. In some implementations, an electrode array may be used to generate localized electrode potentials which selectively cleave linkers bound to the activated electrode. Uses for the linkers include attachment of blocking groups to nucleotides in enzymatic oligonucleotide synthesis.

21 Claims, 18 Drawing Sheets

(56) References Cited

OTHER PUBLICATIONS

Loakes, David, "Survey and Summary: The applications of universal DNA base analogues", In Journal of Nucleic Acids Research, vol. 29, Issue 12, Jun. 15, 2001, pp. 2437-2447.
Carey, et al., "Organic Chemistry", In Publication of MC Graw Hill Education, 2019, 1423 Pages.
Peter G. M. Wuts, "Greene's Protective Groups in Organic Synthesis", In Publication of John Wiley & Sons, Inc., Aug. 11, 2014, 1399 Pages.
Skoog, et al., "Principles of Instrumental Analysis", In Publication of Cengage Learning, Jan. 1, 2017, 985 Pages.
Kissinger, et al., "Cyclic voltammetry", In Journal of chemical education, vol. 60, No. 9, Sep. 1983, pp. 702-706.
Non-Final Office Action mailed on Mar. 20, 2024, in U.S. Appl. No. 18/157,449, (MS# 409297-US03-DIV) 7 pages.
Notice of Allowance mailed on Sep. 19, 2024, in U.S. Appl. No. 18/157,449, (MS#409297-US03-DIV) 8 pages.
"Notice of Allowance Issued in U.S. Appl. No. 17/162,546", Mailed Date: Jan. 25, 2023, 7 Pages.

\* cited by examiner

STRUCTURE 1 METHOXYBENZYL ALCOHOL

STRUCTURE 2. DIMETHOXYBENZYL ALCOHOL

STRUCTURE 5. PROPARGYL THIOESTER

STRUCTURE 6: TRICHLOROETHYL ESTER

US 12,281,134 B2

1

ELECTROCHEMICALLY-CLEAVABLE LINKERS

BACKGROUND

Cleavable linker molecules are used in a variety of biotechnology applications. Linkers couple two molecular entities together with a strong, typically covalent, bond. Cleavage of a linker allows the two entities to separate from each other. The separation can be used to release a molecular entity from attachment to a substrate, trigger a reaction, generate a signal, release a blocking group, or for another purpose. There are many types of linkers and many ways to cleave linkers. For example, linkers may be cleaved by exposure to an acid or a base, exposure to specific chemicals, exposure to light, exposure to heat, exposure to electric current, etc. Linkers may be used in organic solvents or in aqueous solutions.

SUMMARY

This disclosure provides structures for electrochemically-cleavable linkers that cleave in solvents at electrochemical potentials below the redox potential of the solvents. The linkers may be used to connect a nucleotide to any of multiple different types of bound groups. For example, the linkers may be used to connect a nucleotide to a peptide, a linked nucleotide, a fluorophore, or a water-soluble group, etc. The linkers include at least one cleavable group that may be a methoxybenzyl alcohol, an ester, a propargyl thioether, or a trichloroethyl ether. The cleavable group may also optionally include an extension that may be carbonyl group, an alkane group, or an alkene group. The linkers may also optionally include a bound group attachment group that connects the bound group to the linker. The linkers may also optionally include one or more flexible extensions such as polyethylene glycol (PEG). The linkers also include a nucleotide attachment group that attaches the linker to the nucleotide.

This disclosure also provides a technique for cleaving a linker in a solvent by creating an electrode potential in the solvent that is less than the redox potential of solvent which results in cleavage of a bond in the linker. Multiple applications for the electrochemically-cleavable linkers provided in this disclosure are also described. For example, the linkers may be used to tether a blocking group to a nucleotide for enzymatic nucleotide synthesis (e.g., terminal deoxynucleotide transferase (TdT) synthesis) or to tether a fluorophore to a nucleotide for use in sequencing-by-synthesis. In some implementations, microelectrodes of an electrode array may be used to create location-specific changes in the electrochemical microenvironment that trigger cleavage of the linkers only on the surface of the electrode array where the electrodes are activated.

This Summary is provided to introduce a selection of concepts in a simplified form that are further described below in the Detailed Description. This Summary is not intended to identify key features or essential features of the claimed subject matter nor is it intended to be used to limit the scope of the claimed subject matter. The term "techniques," for instance, may refer to system(s) and/or method(s) as permitted by the context described above and throughout the document.

BRIEF DESCRIPTION OF THE DRAWINGS

The Detailed Description is set forth with reference to the accompanying figures. In the figures, the left-most digit(s) of a reference number identifies the figure in which the reference number first appears. The use of the same reference numbers in different figures indicates similar or identical items.

DETAILED DESCRIPTION

Figure 1:
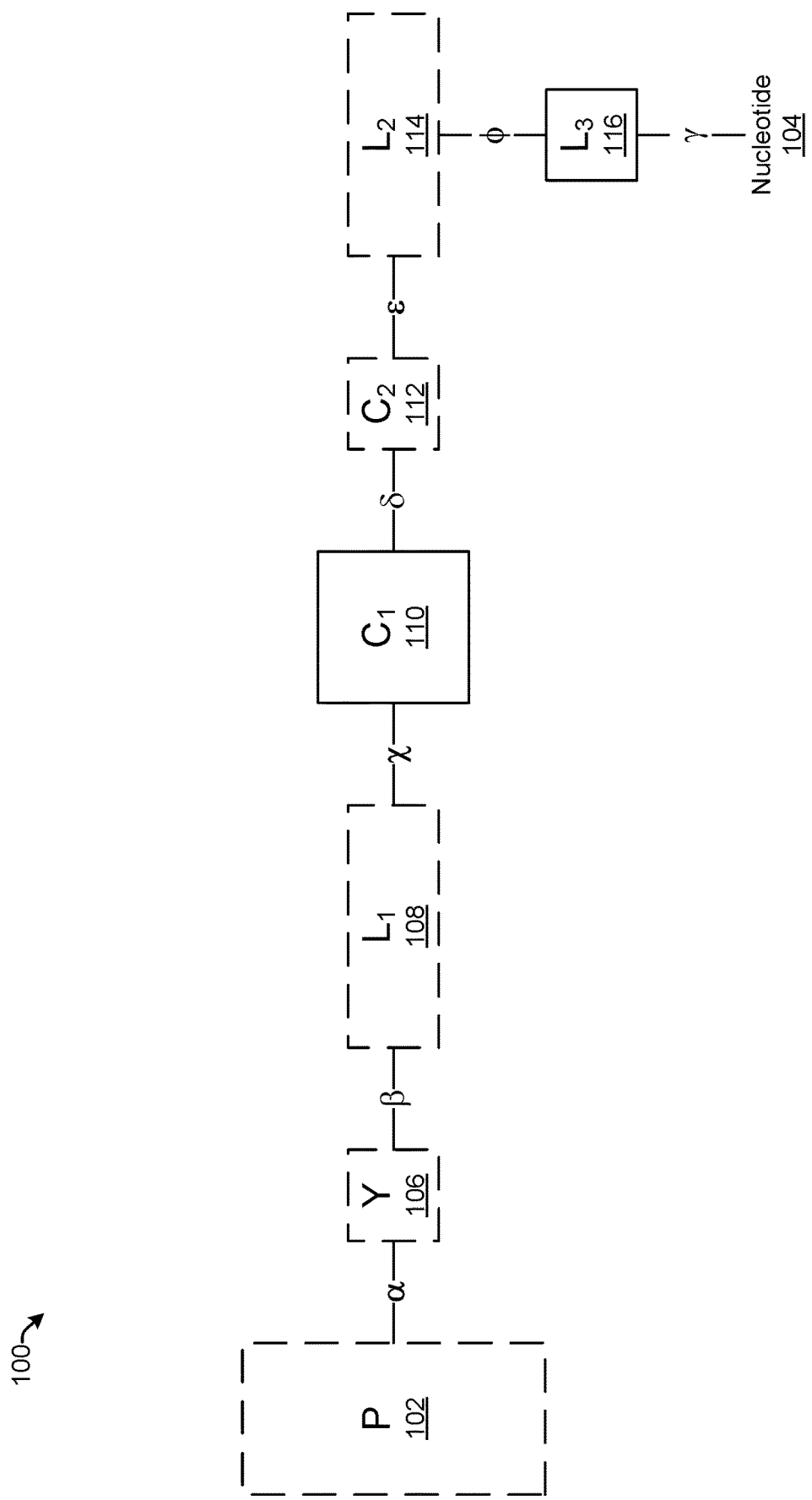
FIG. 1 shows a generalized structure of an electrochemically-cleavable linker. Lowercase Greek letters represent the points of connection between the portions of the linker.

This disclosure provides electrochemically-cleavable linkers that may be used for various applications in liquid solvent environments. Solvents include organic solvents such acetonitrile, N,N-dimethylformamide, N,N-dimethyl-acetamide, dimethylsulfoxide, and methanol. Solvents also include aqueous solvents such as a potassium phosphate buffer and water. Many electrochemically-cleavable linkers are unsuitable for use in certain solvents because the electrode potential required to cleave the linker exceeds the redox potential of the solvent. Thus, the energy from the electrode potential is partially or wholly used to reduce or oxidize the molecules of the solvent rather than to cleave the linkers.

Aqueous environments are particularly challenging to work in because there is only a narrow electrochemical window prior to electrolysis of water. Generation of a sufficient electric potential in an aqueous environment (e.g., about −1.23 V under standard conditions) will cause electrolysis of water releasing oxygen gas at the anode and hydrogen gas at the cathode. The actual voltage at which electrolysis of water occurs depends on the specific conditions of the electrochemical cell such as the pH, temperature, and type of electrode. Aqueous environments include water and aqueous solutions as well as mixtures of aqueous solutions and organic solvents.

The electrolysis potential of a solvent in a given electrochemical cell can be identified by testing of a "blank" sample that has only the solvent without a linker. If a blank sample exhibits electrolysis at a voltage that is higher than a sample containing a linker, then it can be appreciated that cleavage of the linker will occur at a voltage lower than the redox potential of the solvent.

The linkers provided in this disclosure include cleavable groups with oxidation or reduction potentials of less than the redox potential of the solvents in which they are used. In some applications, the solvent may be an aqueous solvent and the redox potential may be the hydrolysis potential of water. The linkers may also include additional groups that increase the water solubility of the linkers. The incorporation of polar functional groups, such as the alcohol, amine, amide, carboxylic acid, sulfonic acid, and phosphate groups, which either ionize or are capable of relatively strong intermolecular forces of attraction with water (hydrogen bonding) are used to increase water solubility.

Electrochemically-cleavable linkers are cleaved by addition of electrons to a bond in the linker. The electrons may be generated by activating an electrode in the proximity of the bond in the linker that is to be cleaved. This may be referred to as a "directly mediated cleavage" in which activation of the electrode, or other change in the local environment, directly causes cleavage of a bond in the linker. Directly electrochemically-cleavable linkers may include a methoxybenzyl alcohol, an ester, a propargyl thioether, or a trichloroethyl ether that when released can trigger an inter-molecular fragmentation reaction thereby cleaving the linker.

Another technique for inducing cleavage due to change in the local conditions may be referred to as "indirectly mediated cleavage." With indirectly mediated cleavage the change in the local conditions caused by activation of an electrode activates an auxiliary molecule which in turn causes cleavage of a bond in the linker. For example, electrochemical generation of a base can promote hydrolysis and cleavage of an ester, and electrochemically generated $Pd^0$ can promote cleavage of a propargyl thioether. Also, electron transfer agents such as ceric ammonium nitrate, 2,3-dichloro-5,6-dicyano-1,4-benzoquinone, or similar are mediator molecules that can be oxidized electrochemically and then facilitate electron transfer to a methoxybenzyl alcohol resulting in cleavage. Vitamin $B_{12}$ is an example of a mediator molecule that can be reduced electrochemically and then facilitate electron transfer to a trichloroethyl ether resulting in cleavage.

If electrochemically-cleavable linkers are anchored to a substrate rather than free in solution, changing the voltage microenvironment on the surface of the substrate can selectively cleave some but not all of the linkers. An electrode array that includes multiple spatially-addressable electrodes may be used to selectively cleave electrochemically-cleavable linkers anchored to the surface of the electrode array. Each electrode may be independently addressable allowing the creation of arbitrary and variable voltage microenvironments across the surface of the electrode array. The microelectrode density may be approximately 1000 microelectrodes/$cm^2$, approximately 10,000 microelectrodes/$cm^2$, or a different density. One example of an electrode array is provided in Bo Bi et al., *Building Addressable Libraries: The Use of "Safety-Catch" Linkers on Electrode arrays*, 132 J. Am. Chem. Soc. 17,405 (2010). One example of a suitable electrode array with microelectrodes is provided in U.S. patent application Ser. No. 16/435,363 filed on Jun. 7, 2019, with the title "Reversing Bias in Polymer Synthesis Electrode Array."

The electrodes may be embedded in solid material from which the electrode array is formed. The electrodes in an electrode array may be implemented using complementary metal-oxide-semiconductor (CMOS) integrated circuits. CMOS circuits use a combination of p-type and n-type metal-oxide-semiconductor field-effect transistors (MOSFETs) to implement logic gates and other digital circuits. The MOSFETs may be made through any conventional manufacturing process including, but not limited to, a triple-well process or a silicon-on-insulator (SOI) process. Although CMOS logic can be implemented with discrete devices for demonstrations, commercial CMOS products are integrated circuits composed of up to billions of transistors of both types, on a rectangular piece of silicon of between 10 and 400 $mm^2$. A series of controllable gates/transistors implemented with CMOS circuits can be controlled to inject charge at any location on the electrode array.

One use for the electrochemically-cleavable linkers of this disclosure is to attach a blocking group to nucleotides for enzymatic nucleotide synthesis. Enzymatic nucleotide synthesis is a technique for synthesizing polynucleotides using template-independent polymerases such as TdT and tRNA nucleotidyltransferase. Enzymatic nucleotide synthesis is performed in aqueous environments in contrast to traditional phosphoramidite synthesis that is performed in the organic solvent acetonitrile.

The polymerase TdT adds nucleotides indiscriminately to the 3' hydroxyl group at the 3' end of single-stranded DNA. Because TdT performs unregulated synthesis, use of this enzyme to create a polynucleotide with a pre-specified arbitrary sequence requires regulation and control of the TdT activity. One way to force single-nucleotide addition is to attach a blocking group to each nucleotide so that once it is incorporated is not possible for the enzyme to add additional nucleotides until the blocking group is removed. The TdT enzyme itself may be attached to a nucleotide with the linker so that the enzyme acts as its own blocking group. See Sebastian Palluck et al., *De novo DNA synthesis using polymerase-nucleotide conjugates*, 36(7) Nature Biotechnology 645 (2018) and WO 2017/223517 A1. The linkers used by Palluck et al. are not electrochemically-cleavable linkers but rather they are photo-cleavable linkers and chemically-cleavable linkers.

Currently known template-independent polymerases include TdT and tRNA nucleotidyltransferase. TdT includes both the full-length wild-type enzyme, as well as modified enzymes that are truncated or internally modified. One example of modified TdT is provided in U.S. Pat. No. 10,059,929. An example of truncated TdT is provided in U.S. Pat. No. 7,494,797. Thus, template-independent polymerase as used herein includes full-length wild-type, truncated, or otherwise modified TdT, tRNA nucleotidyltransferase, and any subsequently discovered or engineered polymerases that can perform template-independent synthesis of polynucleotides. Template independent polymerase as used herein does not encompass modifications of TdT or tRNA nucleotidyltransferase that render those enzymes incapable of performing template-independent nucleotide polymerization.

Another use for electrochemically-cleavable linkers is to attach fluorophores to nucleotides for sequencing-by-synthesis. A different colored fluorophore may be conjugated to each variety of nucleotide (e.g., cytosine (C), guanine (G), adenine (A), or thymine (T)) using the linkers provided in this disclosure. The color of the fluorescence may be detected indicating which nucleotide has been incorporated into a growing DNA strand. This application differs from conventional sequencing-by-synthesis techniques in that the linkers are cleaved electrochemically rather than through use of a chemical cleavage agent.

As used herein, polynucleotides, also referred to as oligonucleotides, include both DNA, RNA, and hybrids containing mixtures of DNA and RNA. DNA includes nucleotides with one of the four natural bases cytosine (C), guanine (G), adenine (A), or thymine (T) as well as unnatural bases, noncanonical bases, and/or modified bases. RNA includes nucleotides with one of the four natural bases cytosine, guanine, adenine, or uracil (U) as well as unnatural bases, noncanonical bases, and/or modified bases. Nucleotides include both deoxyribonucleotides and ribonucleotides covalently linked to one or more phosphate groups.

FIG. 1 shows a schematic representation of an illustrative structure of a linker 100. The linker 100 is electrochemically-cleavable at a lower electrochemical potential than the redox potential of the solvent in which the linker is present. The linker 100 may also be water soluble. The linker 100 may be used to attach a bound group or "P group" 102 to a nucleotide 104. The nucleotide 104 may be a DNA or RNA nucleotide with any of the canonical bases—adenine (A), cytosine (C), guanine (G), thymine (T), or uracil (U)—or an artificial or non-canonical base. The nucleotide 104 is attached to one, two, or preferably three phosphate groups. Connecting the P group 102 to the nucleotide 104 are a "Y group" 106, a "$L_1$ group" 108, a "$C_1$ group" 110, a "$C_2$ group" 112, a "$L_2$ group" 114, and a "$L_3$ group" 116. The Y group 106 is a bound group attachment group that attaches the P group 102 the linker 100. The $L_1$ group 108 and the $L_2$ group 114 are flexible extensions. The $C_1$ group 110 is a cleavable group. The $C_2$ group 112 is an extension of the cleavable group. The $L_3$ group 116 is a nucleotide attachment group that attaches the nucleotide 104 to the linker 100.

The P group 102, Y group 106, and $C_2$ group 112 are optional. One of the $L_1$ 108 and $L_2$ groups 114 may be omitted or both may be included. Connections between the groups are represented by the lower-case Greek letters α, β, χ, δ, ε, φ, and γ.

The bound group that is attached to the nucleotide 104 by the linker 100, also called the P group 102, may be a peptide, a linked nucleotide, a fluorophore, or a water-soluble group. As used herein, "peptide" may be either a single peptide or a polypeptide. Polypeptides are two or more amino acids linked in a chain with the carboxyl group of each acid being joined to the amino group of the next by a bond of the type —OC—NH—. Polypeptides include enzymes which are proteins that catalyze biochemical reactions. Examples of enzymes that may be attached as a bound group "P" 102 include DNA polymerases and RNA polymerases such as TdT and tRNA nucleotidyltransferase.

As used herein, a "linked nucleotide" may be any DNA or RNA nucleotide including oligonucleotides having two or more nucleotides with a canonical or non-canonical base. In some implementations, the linked nucleotide is complementary to the nucleotide 104 at the other end of the linker. Thus, the nucleotide 104 can form Watson-Crick base pairing with the linked nucleotide. In some implementations, the linked nucleotide may be a nucleotide without a triphosphate group. Lack of the triphosphate group can prevent a polymerase such as TdT from incorporating the linked nucleotide into a DNA strand.

The linked nucleotide may also be a universal base. A universal base is an artificial nucleotide base that fits inside a DNA double-stranded helix and forms hydrogen bonding with any other base. For example, the universal base may be deoxyinosine (e.g., 2'-deoxyisoinosine, 7-deaza-2'-deoxyinosine, and 2-aza-2'-dexosyinosine), isocarbostyril nucleoside derivatives, or 8-aza-7-deazaadenine. These and other examples of universal bases are discussed in David Loakes, *The Applications of Universal DNA Base Analogues*, 29(12) Nucleic Acids Research 2437 (2001) and the references cited therein. If the linked nucleotide includes a universal base it may also hybridize with the nucleotide 104.

A fluorophore is a fluorescent chemical compound that can re-emit light upon light excitation. Fluorophores typically contain several combined aromatic groups or planar or cyclic molecules with several π bonds. The fluorophore may be, for example, fluorescein (e.g. fluorescein amidite), rhodamine (e.g., Rhodamine 6G, Rhodamine 123, or Rhodamine B), cyanine which refers to a synthetic dye family belonging to polymethine group and includes streptocyanines or open chain cyanines, hemicyanines, and closed chain cyanines (e.g., Cy2, Cy3, Cy3B, Cy3.5, Cy5, Cy5.5, and Cy7 available from GE healthcare); coumarin (2H-chromen-2-one) among the various coumarin laser dyes are coumarins 480, 490, 504, 521, 504T, and 521T; or borondipyrromethene (BODIPY) which is composed of dipyrromethene complexed with a disubstituted boron center, typically $BF_2$. Cleavage of the linker 100 may release the fluorophore generating a detectable fluorescent signal.

As used herein, a "water-soluble group" is any organic (i.e., carbon containing) chemical moiety that is both itself water soluble and if present as the P group 102 causes the linker 100 as a whole structure to be water soluble. One illustrative water-soluble group is glutathione. Many polypeptides and enzymes are also water-soluble groups. A linked nucleotide, especially a nucleotide triphosphate, may be a water-soluble group.

The Y group 106, if present, is a bioconjugation group that is selected based on the structure of the P group 102 so that the Y group 106 can form a covalent bond to one or more atoms in the P group 102. Options for the Y group 106 are shown in the following table.

TABLE 1

Bound Group Attachment Group Structures (Y group 106).

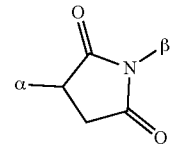

TABLE 1-continued

Bound Group Attachment Group Structures (Y group 106).

α-S-β

α-NH$_2$-β

In Table 1, α represents a point of attachment to the P group 102 and β represents a point of attachment to the L$_1$ group 108 or the C$_1$ group 110 if the L$_1$ group 108 is omitted.

The L$_1$ group 108, if present, creates space between the P group 102 and the C$_1$ group 110 and provides flexibility to the structure of the linker 100. Options for the L$_1$ group 108 are shown in the following table.

TABLE 2

Flexible Extension Structures (L$_1$ group 108).

In Table 2, n is an integer which is between 1-30, 1-20, 1-10, or 1-5; R$_1$ is hydrogen or a substituted or unsubstituted straight or branched alkyl group having 1 to 6 carbon atoms; β represents a point of attachment to the Y group 106, if present, to the or P group 102; and χ represents a point of attachment to the C$_1$ group 110. Examples of suitable flexible extension structures include polyethylene glycol (PEG) and methylene. For example, the flexible extension structure may be a PEG trimer but it could also be a longer or shorter PEG structure.

The C$_1$ group 110 is a cleavable group that decomposes in response to application of an electrode potential that is less than the redox potential of the solvent such as less than the hydrolysis potential of water. Options for the C$_1$ group 110 are shown in the following table.

TABLE 3

Cleavable Group Structures (C$_1$ group 110).

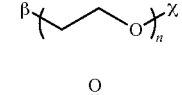

X$_1$ is 1 to 4 ring substituents consisting of a hydrogen, a hydroxyl group, an ether group with an alkyl group having 1 to 3 carbon atoms, an amine group which is unsubstituted or substituted with one or two alkyl groups having 1 to 2 carbon atoms, an alkyl group having 1 to 2 carbon atoms, or a halogen.
X$_2$ is hydrogen, a methyl group, an ethyl group, or an isopropyl group.

In Table 3, χ represents a point of attachment to the Li group 108, the Y group 106, or the P group 102 and δ represents a point of attachment to the C$_2$ group 112, the L$_2$ group 114, or the L$_3$ group 116.

The C$_2$ group 112 is an extension of the C$_1$ group 110 that may be present or omitted. Options for the C$_2$ group 112 are shown in the following table.

TABLE 4

Cleavable Group Extension Structures (C$_2$ group 112).

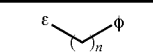

R$_2$ is hydrogen or a substituted or unsubstituted straight or branched alkyl group having 1 to 6 carbon atoms In Table 4, δ represents a point of attachment to the C$_1$ group 110 and ε represents a point of attachment to the L$_2$ group 114 or the L$_3$ group 116.

TABLE 5

Flexible Extension Structures (L$_2$ group 114).

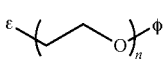

In Table 5, n is an integer which is between 1-30, 1-20, 1-10, or 1-5; R$_1$ is hydrogen or a substituted or unsubstituted straight or branched alkyl group having 1 to 6 carbon atoms; ε represents a point of attachment to the C$_2$ group 112, if present, or to the $C_1$ group 110; and φ represents a point of attachment to the $L_3$ group 116.

The $L_3$ group 116 is a nucleotide attachment group that connects the linker 100 to the nucleotide. Options for the $L_3$ group 116 are shown in the following table.

TABLE 6

Nucleotide Attachment Group Structures ($L_3$ group 116).

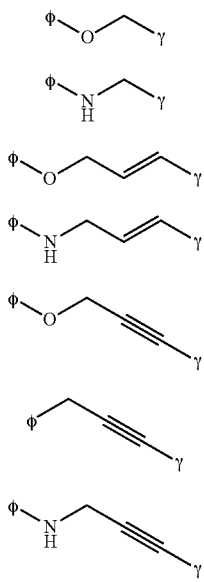

In Table 6, φ represents a point of attachment to the $C_1$ group 110, the $C_2$ group 112, or the $L_2$ group 114 and γ represents a point of attachment to the nucleotide. In some implementations, the $L_3$ group 116 attaches to the base of the nucleotide. If the base is a purine base (i.e., adenosine or guanine), the $L_3$ group 116 may attach to the number 7 nitrogen of the purine base. If the base is a pyrimidine base (i.e., cytosine, thymine, or uracil), the $L_3$ group 116 may attach to the number 5 carbon of the pyrimidine base.

Figure 2:
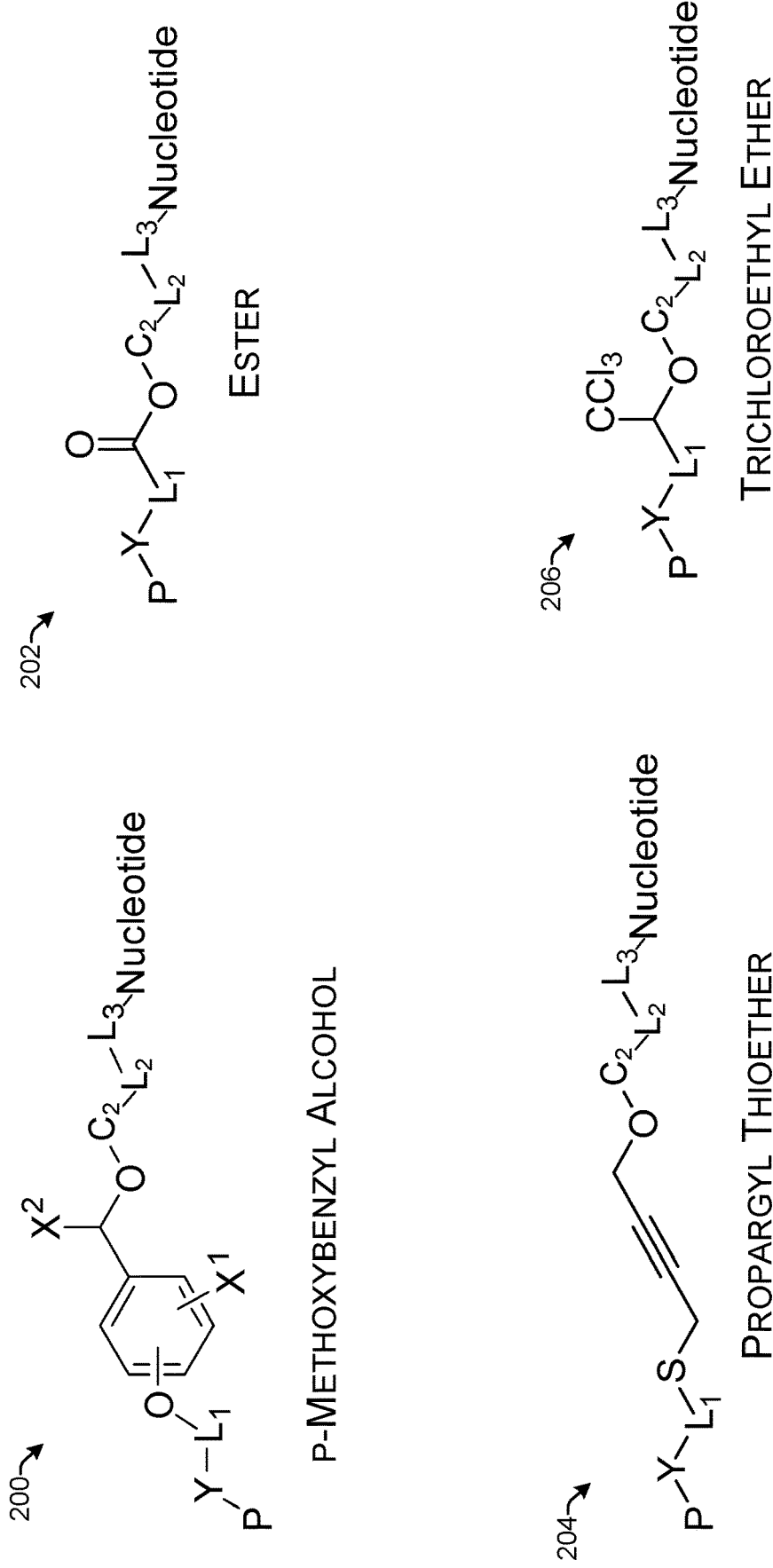
FIG. 2 shows structures of electrochemically-cleavable linkers that illustrate four different types of cleavable groups.

FIG. 2 shows generalized structures of linkers with four different examples of specific cleavable groups. All of the linkers shown in FIG. 2 are specific examples of the general linker structure of linker 100 shown in FIG. 1. A methoxybenzyl alcohol linker 200 has a methoxybenzyl alcohol as the $C_1$ group 110 with p being 1, 2, or 3. Without being bound by theory, it is believed that increasing number of oxygen groups attached to the benzyl ring reduces the electrode potential necessary to cleave the linker. An ester linker 202 has an ester group as the $C_1$ group 110. A propargyl thioether linker 204 has a propargyl thioether group as the $C_1$ group 110. A trichloroethyl ether linker 206 has a trichloroethyl ether group as the $C_1$ group 110.

Figure 3:
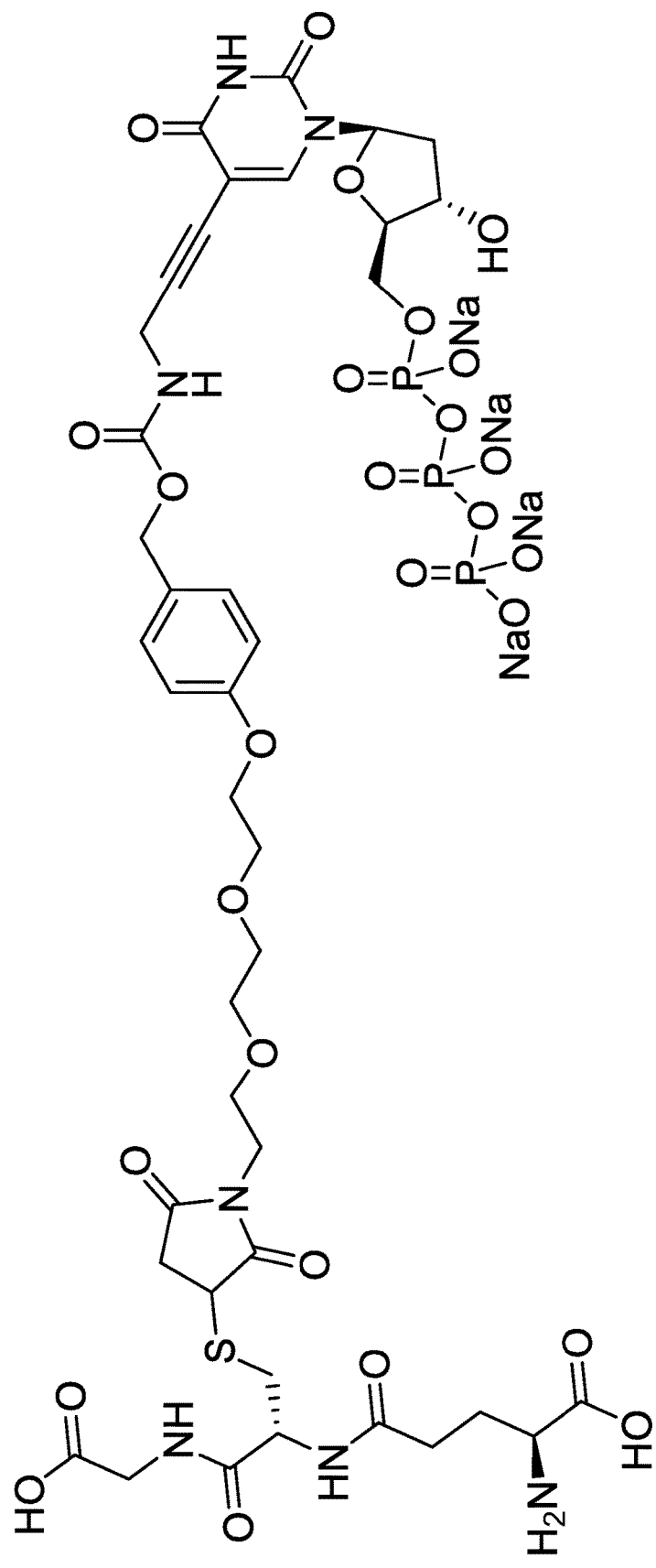
FIG. 3 shows the structure of a first example linker with a methoxybenzyl alcohol cleavable group.

FIG. 3 illustrates an example linker 300 referred to as Structure 1 that has a methoxybenzyl alcohol $C_1$ group 110. This linker 300 is a specific example of the methoxybenzyl alcohol linker 200 shown in FIG. 2. The P group 102 is shown as glutathione, but this is merely illustrative, and glutathione may be replaced with any of the other options for the P group 102. The nucleotide 104 is shown as deoxyribose thymine triphosphate, but this is merely illustrative, and deoxyribose thymine triphosphate may be replaced with any other nucleotide 104. In this example linker 300, the flexible extension $L_2$ group 114 is omitted.

Figure 4:
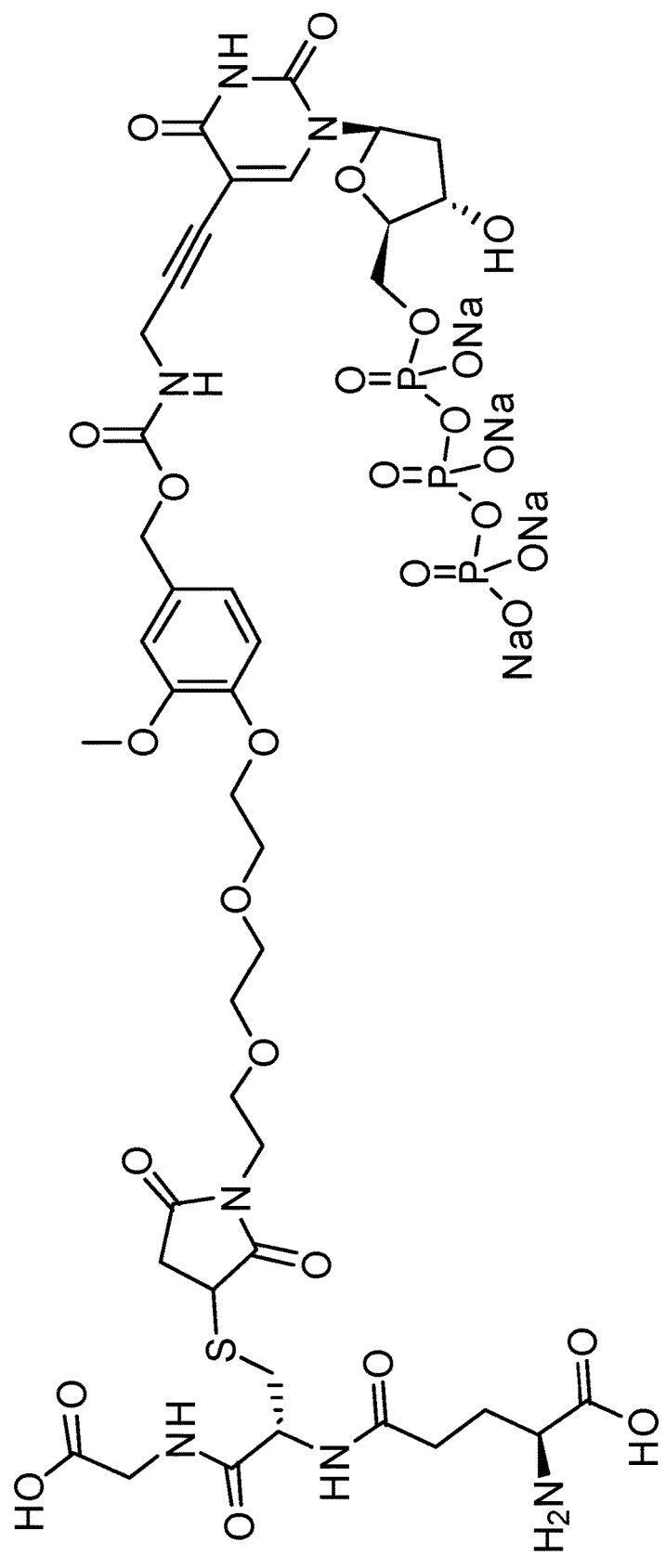
FIG. 4 shows the structure of a second example linker with a dimethoxybenzyl alcohol cleavable group.

FIG. 4 illustrates an example linker 400 referred to as Structure 2 that has a dimethoxybenzyl alcohol $C_1$ group 110. This linker 400 is a specific example of the methoxybenzyl alcohol linker 200 shown in FIG. 2. The P group 102 is shown as glutathione, but this is merely illustrative, and glutathione may be replaced with any of the other options for the P group 102. The nucleotide 104 is shown as deoxyribose thymine triphosphate but this is merely illustrative and deoxyribose thymine triphosphate may be replaced with any other nucleotide 104. In this example linker 400, the flexible extension $L_2$ group 114 is omitted.

Figure 5:
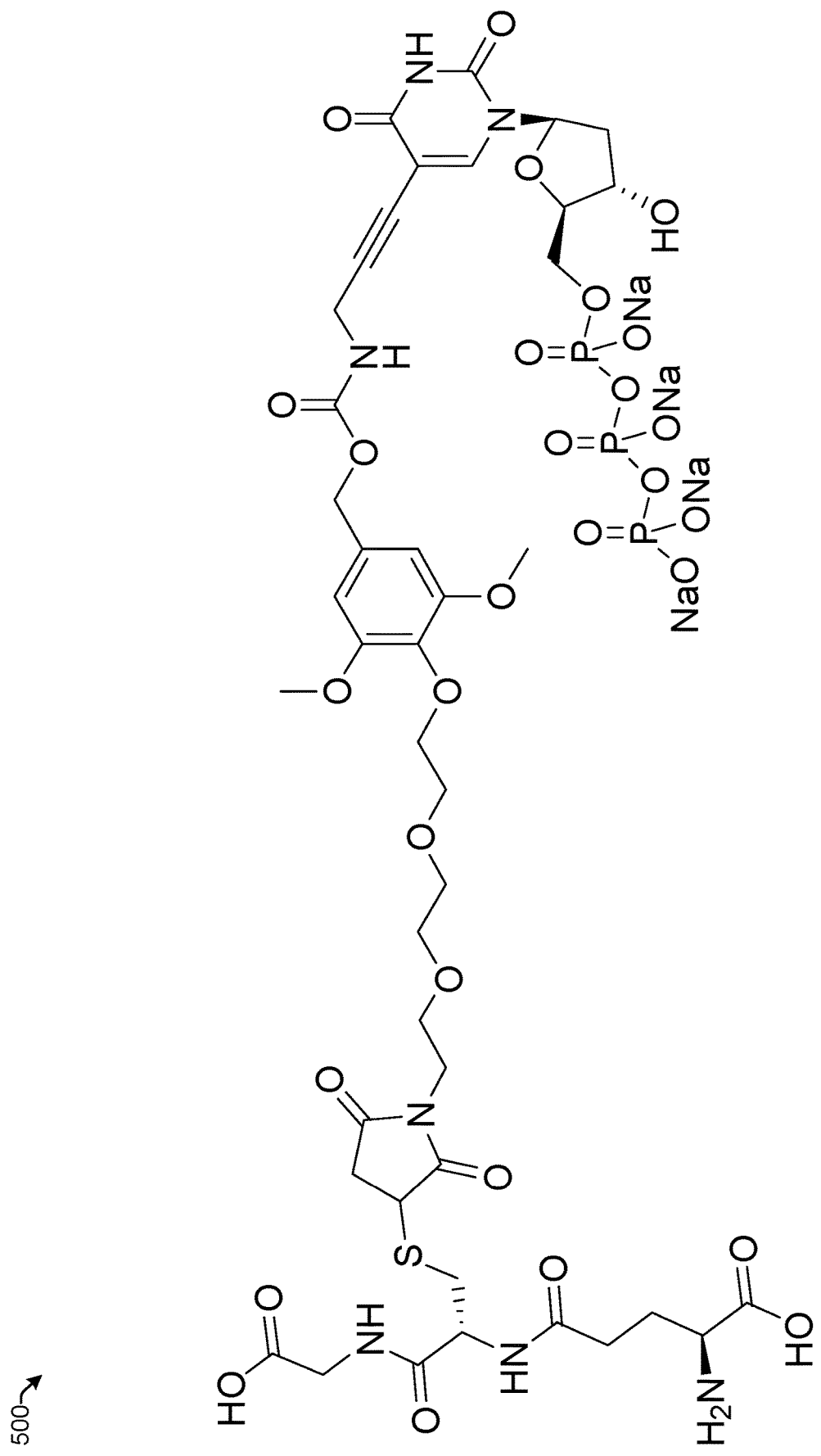
FIG. 5 shows the structure of a third example linker with a trimethoxybenzyl alcohol cleavable group.

FIG. 5 illustrates an example linker 500 referred to as Structure 3 that has a trimethoxybenzyl alcohol $C_1$ group 110. This linker 500 is a specific example of the methoxybenzyl alcohol linker 200 shown in FIG. 2. The P group 102 is shown as glutathione, but this is merely illustrative, and glutathione may be replaced with any of the other options for the P group 102. The nucleotide 104 is shown as deoxyribose thymine triphosphate, but this is merely illustrative, and deoxyribose thymine triphosphate may be replaced with any other nucleotide 104. In this example linker 500, the flexible extension $L_2$ group 114 is omitted.

Figure 6:
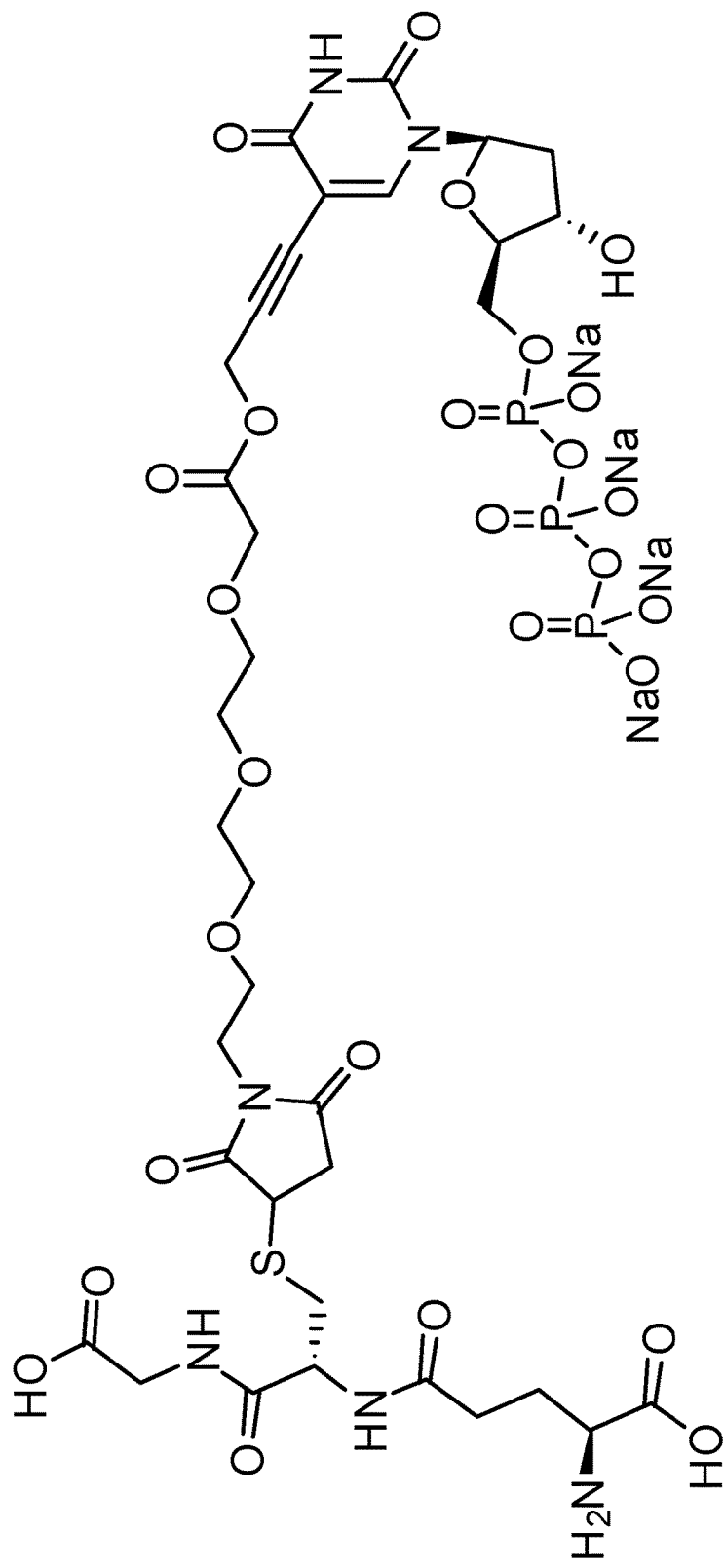
FIG. 6 shows the structure of a fourth example linker with an ester cleavable group.

FIG. 6 illustrates an example linker 600 referred to as Structure 4 that has an ester $C_1$ group 110. This linker 600 is a specific example of the ester linker 202 shown in FIG. 2. The P group 102 is shown as glutathione, but this is merely illustrative, and glutathione may be replaced with any of the other options for the P group 102. The nucleotide 104 is shown as deoxyribose thymine triphosphate, but this is merely illustrative, and deoxyribose thymine triphosphate may be replaced with any other nucleotide 104. In this example linker 600, the flexible extension $L_2$ group 114 is omitted.

Figure 7:
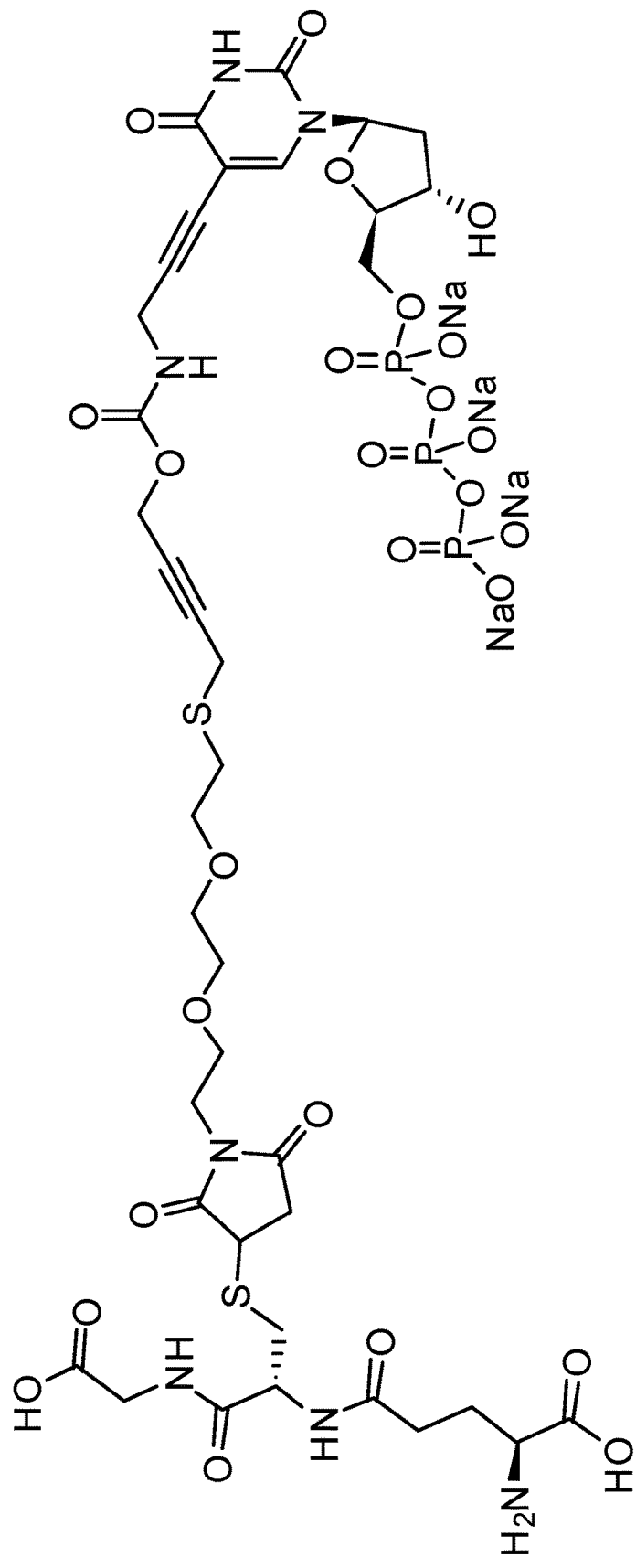
FIG. 7 shows the structure of a fifth example linker with a propargyl thioether cleavable group.

FIG. 7 illustrates an example linker 700 referred to as Structure 5 that has a propargyl thioether $C_1$ group 110. This linker 700 is a specific example of the propargyl thioether linker 204 shown in FIG. 2. The P group 102 is shown as glutathione, but this is merely illustrative, and glutathione may be replaced with any of the other options for the P group 102. The nucleotide 104 is shown as deoxyribose thymine triphosphate, but this is merely illustrative, and deoxyribose thymine triphosphate may be replaced with any other nucleotide 104. In this example linker 700, the flexible extension $L_2$ group 114 is omitted.

Figure 8:
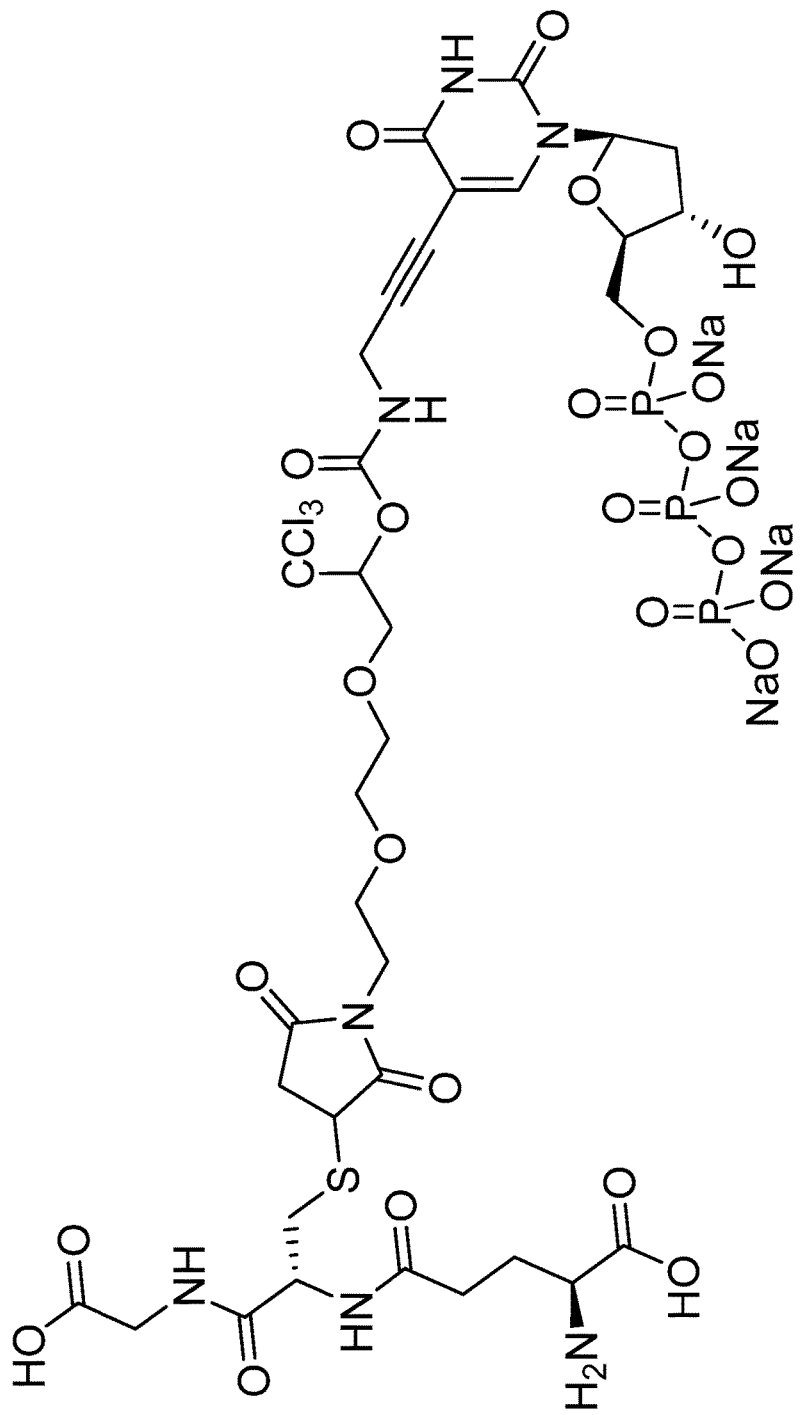
FIG. 8 shows the structure of a sixth example linker with a trichloroethyl ester cleavable group.

FIG. 8 illustrates an example linker 800 referred to as Structure 6 that has a trichloroethyl ester $C_1$ group 110. This linker 800 is a specific example of the trichloroethyl ester linker 206 shown in FIG. 2. The P group 102 is shown as glutathione, but this is merely illustrative, and glutathione may be replaced with any of the other options for the P group 102. The nucleotide 104 is shown as deoxyribose thymine triphosphate, but this is merely illustrative, and deoxyribose thymine triphosphate may be replaced with any other nucleotide 104. In this example linker 800, the flexible extension $L_2$ group 114 is omitted.

Figure 9:
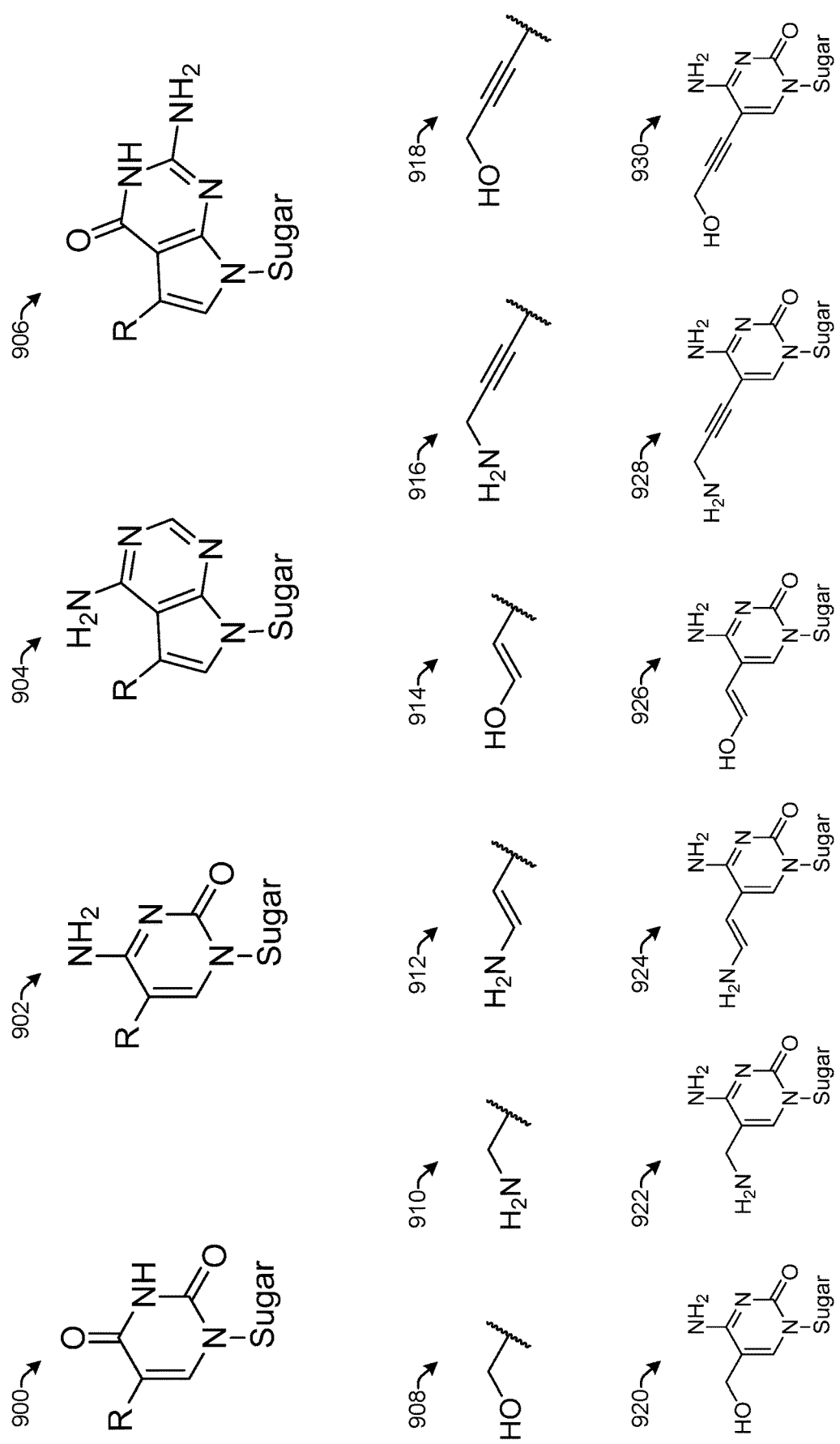
FIG. 9 shows example points of attachment to bases of nucleotides and scars left on nucleotide bases following cleavage of a linker.

FIG. 9 shows examples of points of attachment of linkers to bases of nucleotides and the scars left after cleavage of a linker. The nucleotide bases thymine/uracil 900, cytosine 902, adenine 904, and guanine 906 are shown with R representing the point of attachment to a linker and "sugar" representing the sugar group of the nucleotide. In these examples, the linker is connected to the number 7 nitrogen of the purine bases (i.e., adenosine or guanine) and the number 5 carbon of the pyrimidine bases (i.e., cytosine, thymine, or uracil).

Examples of the $L_3$ group 116 following cleavage of the linker are shown as structures 908, 910, 912, 914, 916, and 918. Any of these structures may be present in place of the R group shown on the nucleotide bases 900, 902, 904, and 906. Examples structures in which cytosine is shown attached to each of the examples of the $L_3$ group 116 are shown 920, 922, 924, 926, 928, and 930. Cytosine is merely illustrative and may be replaced with any of the other nucleotide bases. These structures 920, 922, 924, 926, 928, and 930 represent the scars left on a nucleotide after cleavage of a linker. The scar terminates in a hydroxyl group or an amide group. If the nucleotide 104 is part of an oligonucleotide the scar may be removed, if necessary, through polymerase chain reaction (PCR) amplification. Copies of the single-stranded DNA created by PCR amplification can be created using nucleosides that do not have scars. Thus, none of the population of double-stranded DNA molecules created by PCR would have scars except for the single molecule that incorporates the original nucleotide.

Figure 10:
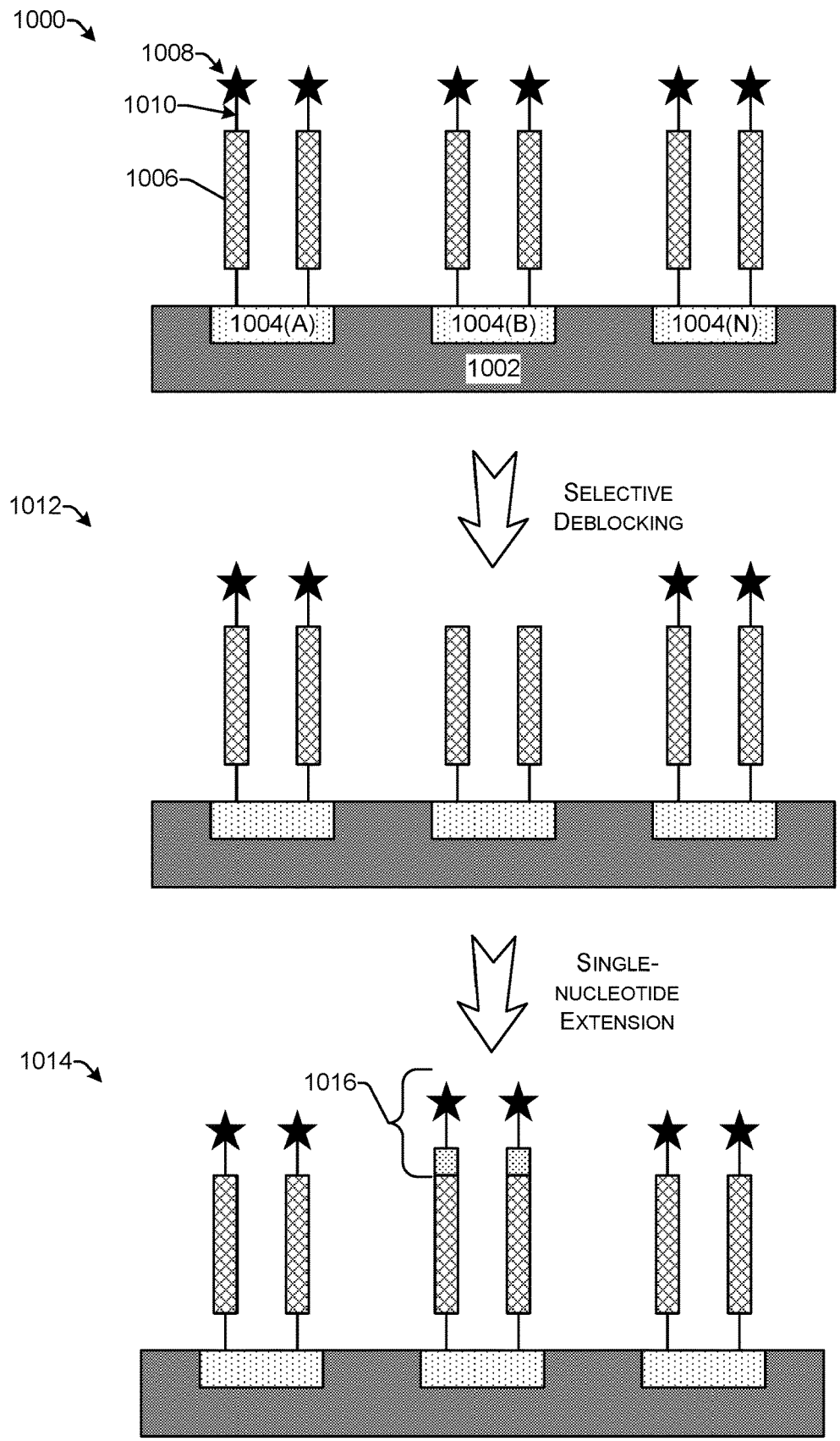
FIG. 10 shows a time series of steps in enzymatic nucleotide synthesis using single nucleotides attached to protecting groups by a linker.

FIG. 10 shows an example time series of steps in enzymatic nucleotide synthesis. A configuration at a first time point 1000 shows an electrode array 1002 containing multiple microelectrodes 1004(A), 1004(B), . . . , 1004(N) coated with single-stranded oligonucleotides 1006 capped by blocking groups 1008 attached to a terminal nucleotide via a linker 1010. The linker 1010 may be any of the electrochemically cleavable linkers provided in this disclosure. The blocking group 1008 is one option for the P group 102 shown in FIG. 1. The blocking group 1008 prevents template-independent polymerases such as TdT from adding more than a single nucleotide during each round of synthesis.

In one implementation, the enzyme TdT itself may be used as the blocking group 1008. A technique for using TdT as a blocking group to force single-nucleotide addition with enzymatic nucleotide synthesis is described in Sebastian Palluck et al., De novo DNA synthesis using polymerase-nucleotide conjugates, 36(7) Nature Biotechnology 645 (2018) and WO 2017/223517 A1.

The blocking group 1008 may, in some implementations, be a linked nucleotide, including a short oligonucleotide (e.g., 2-10 bp), that is complementary to the nucleotide at the 3' end of the oligonucleotide 1006. The complementary relationship may result in hybridization which can cause the two nucleotides joined by the linker 1010 to form a loop or hairpin structure. This prevents addition of other nucleotides onto the 3' end of the oligonucleotide 1006. As an alternative to a complementary nucleotide, the linked nucleotide may be a nucleotide that includes one or more universal bases. The universal bases can hybridize with any other nucleotide in oligonucleotide 1006 and may form a similar loop or hairpin structure.

A second time point 1012, shows selective deblocking of some but not all of the oligonucleotides 1006 attached to the surface of electrode array 1002. Activation of one of the microelectrodes such as 1004(B) selectively triggers cleavage of the linkers 1010 attached to that microelectrode 1004(B) without cleaving linkers 1010 attached to any of the other microelectrodes 1004 on the surface of the electrode array 1002. Cleavage of the linkers 1010 releases the blocking groups 1008 so that nucleotide extension may occur on the deblocked oligonucleotides. If the blocking group 1008 is a complementary nucleotide or nucleotides with a universal base, the hydrogen bonds responsible for base pairing or unlikely to be sufficiently strong to keep the nucleotide hybridize to the oligonucleotide strand 1006 once the linker 1010 is cleaved. However, the temperature of the electrodes cell may be elevated to promote disassociation.

A third time point 1014, shows single nucleotide extension of the unblocked oligonucleotides 1006 by addition of nucleotide-blocking group structures 1016 with an electrochemically-cleavable linker 1010 that attaches the nucleotide to the blocking group 1008. The nucleotides included in the nucleotide-blocking group structures 1016 are joined to the end of the unblocked oligonucleotides by the action of a polymerase or ligase. This process may then be repeated with selective addition of single nucleotides at locations on the electrode array 1002 that are selectively deblocked by activation of the corresponding microelectrodes 1004. By repeating this series of steps, multiple different oligonucleotides may be synthesized on the surface of the electrode array by repeated single-nucleotide addition.

Figure 11:
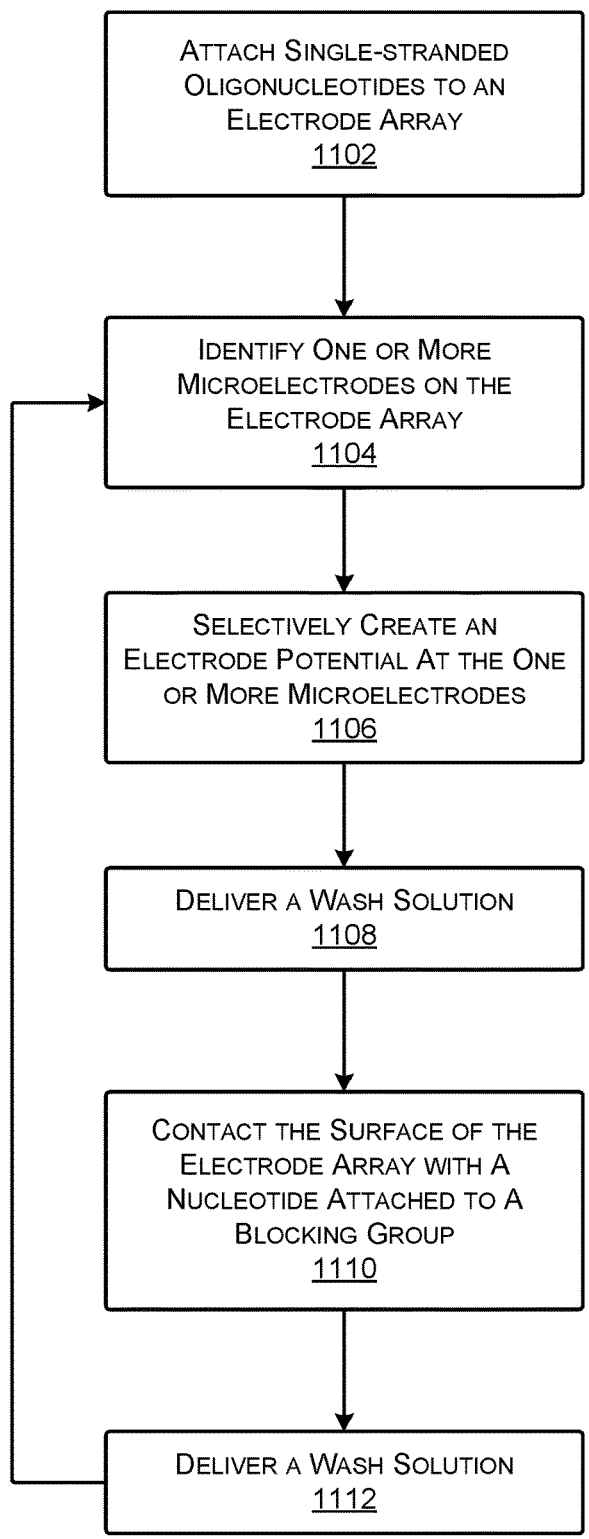
FIG. 11 is a flow diagram of an illustrative process for enzymatic nucleotide synthesis.

FIG. 11 shows a process 1100 for enzymatic nucleotide synthesis. Process 1100 may be implemented using any of the linkers shown in FIGS. 1-8. FIG. 10 illustrates some of the steps of process 1100.

At operation 1102, single-stranded oligonucleotides are attached to the surface of an electrode array. This results in the creation of an electrode array that is covered with a plurality of oligonucleotides. The surface of the electrode array is inside of an electrochemical cell. The electrochemical cell is filled with an aqueous solution such as a buffered solution for use with a template-independent polymerase. The oligonucleotides are single-stranded molecules with a length of between about 3-30 nucleotides. A template-independent polymerase uses the polynucleotides as a starting point for enzymatic polynucleotide synthesis by adding additional nucleotides to the 3' terminal nucleotides at the end of the original, bound oligonucleotides.

At operation 1104, one or more microelectrodes on the electrode array are identified. The microelectrodes may be identified by a computer system that tracks the sequence in which the microelectrodes have been activated and that controls activation of the microelectrodes according to programmatic instructions. The programmatic instructions may be designed to synthesize multiple oligonucleotides with specific, predetermined sequences according to techniques known to those of skill in the art.

At operation 1106, an electrode potential is selectively created at one or more of the microelectrodes. The change in electrode potential may positive or negative and has a magnitude that is less than the hydrolysis potential of water. The electrode potential cleaves the linkers attached to blocking groups on the 3' ends of the oligonucleotides attached to the surface of the electrode array. The electrode potential in the proximity of other electrodes that are not activated does not change or changes only to a degree that does not cause cleavage of the linkers. This provides selective deblocking of some but not all of the nucleotides attached to the surface of the electrode array.

At operation 1108, a wash solution is delivered to the surface of the electrode array. The wash solution may be flowed across the entire surface of the electrode array. This washing step can remove any of the blocking groups that are in solution following cleavage of the linkers. The wash solution may be water without added salts or an aqueous solution that contains at least one of a salt or a buffer. The buffer may be any one of a number of aqueous buffers that are compatible with polymerases and single-stranded nucleotides such as PBS or tris-buffered saline (TBS).

At operation 1110, the surface of the electrode array is contacted with a predetermined nucleotide attached to a blocking group via an electrochemically-cleavable linker with a cleavage potential less than the hydrolysis potential of water. The electrochemically-cleavable linker may be the linker 100 shown in FIG. 1. For example, the nucleotide may be one of deoxyadenosine triphosphate (dATP), deoxycytidine triphosphate (dCTP), deoxyguanosine triphosphate (dGTP), deoxythymidine triphosphate (dTTP), adenosine triphosphate (ATP), cytidine triphosphate (CTP), guanosine triphosphate (GTP), or uridine triphosphate (UTP). The nucleotide may be provided in a nucleotide solution that contains only a single type of nucleotide and a template-independent polymerase in an appropriate buffer solution. During operation 1110 the template-independent polymerase adds the nucleotide to the deblocked 3' ends of the oligonucleotides.

The blocking group is an entity that when attached to the nucleotide prevents a polymerase from adding additional nucleotides to nucleotide that is linked to the blocking group. The blocking group may be the polymerase enzyme itself, such as TdT, or a linked nucleotide that hybridizes to the nucleotide added on to the end of an oligonucleotide attached to the surface of the electrode array. The linked nucleotide may be a complementary nucleotide or a nucleotide with a universal base either of which can hybridize to the nucleotide thereby preventing the action of the polymerase.

At operation 1112, a wash solution is delivered to the surface of the electrode array. The wash solution may remove unreacted nucleotides and enzymes. This prevents the incorporation of an incorrect nucleotide during a subsequent cycle of synthesis. The wash solution may be without added salts or an aqueous solution that contains at least one of a salt or a buffer. The buffer may be any one of a number of aqueous buffers that are compatible with polymerases and single-stranded nucleotides such as PBS or TBS. The wash solution used at operation 1112 may be the same as the wash solution used at operation 1108.

Process 1100 may iteratively repeat by returning to operation 1104 until oligonucleotides with the desire sequences are fully synthesized. Each subsequent iteration of synthesis may add a different nucleotide at a different set of locations depending on which oligonucleotides have been unblocked by activation of specific electrodes. Repeating this process while varying the nucleotide added and the locations at which the blocking groups are removed makes it possible to create multiple different oligonucleotide sequences with single-base specificity using a template-independent polymerase.

EXAMPLES

The following examples show the results of cyclic voltammetry experiments performed on electrochemical cells containing various linkers. Cyclic voltammetry is an electrochemical technique that measures the current that develops in an electrochemical cell under conditions where voltage is in excess of that predicted by the Nernst equation. Cyclic voltammetry is performed by cycling the potential of a working electrode and measuring the resulting current against a reference electrode which maintains a constant potential.

In a cyclic voltammetry experiment, the working electrode potential is ramped linearly versus time. Unlike in linear sweep voltammetry, after the set potential is reached in a CV experiment, the working electrode's potential is ramped in the opposite direction to return to the initial potential. The current at the working electrode is plotted versus the applied voltage (i.e., the potential of the working electrode) to give the cyclic voltammogram trace. Techniques for performing cyclical voltammetry experiments are known to those of ordinary skill in the art and may be found in Skoog, D.; Holler, F.; Crouch, S. *Principles of Instrumental Analysis* (2007) and Kissinger, P. T., Heineman, W. R., *Cyclic Voltammetry*, 60 J. of Chem. Education, 702 (1983). In all the following examples electrode potential is measured in volts (V) relative to a reference electrode and the current is measured in amperes (A).

Figure 12:
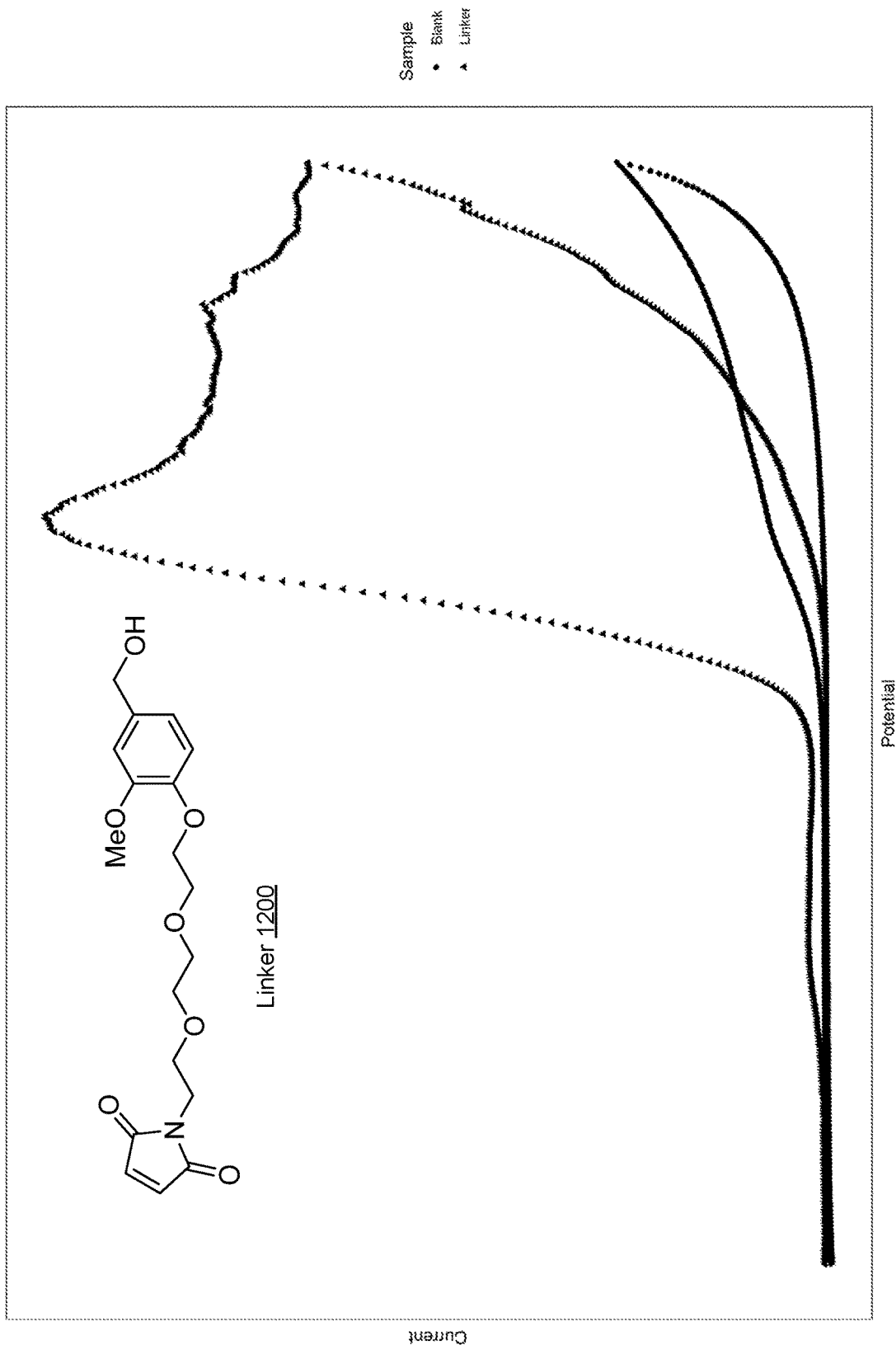
FIG. 12 is a cyclic voltammogram trace showing change in current as the electrode potential is varied in a buffered solution containing a linker with Structure 1 shown in FIG. 4.

FIG. 12 shows a cyclic voltammogram trace for 20 mM of a linker 1200 with a cleavable group that is the same as in Structure 2 shown in FIG. 4 compared to a blank electrochemical cell containing the same solvent. The linker 1200 differs from Structure 2 because it does not include the groups P, $C_2$, $L_2$, $L_3$, or a nucleotide. The electrode potential was generated with a 12.5 mm$^2$ platinum working electrode and a platinum counter electrode using a 10 mV/s sweep rate. The linker 1200 exhibits a pronounced anodic peak indicating cleavage of the linker. There is no similar anodic peak potential in the blank sample.

Figure 13:
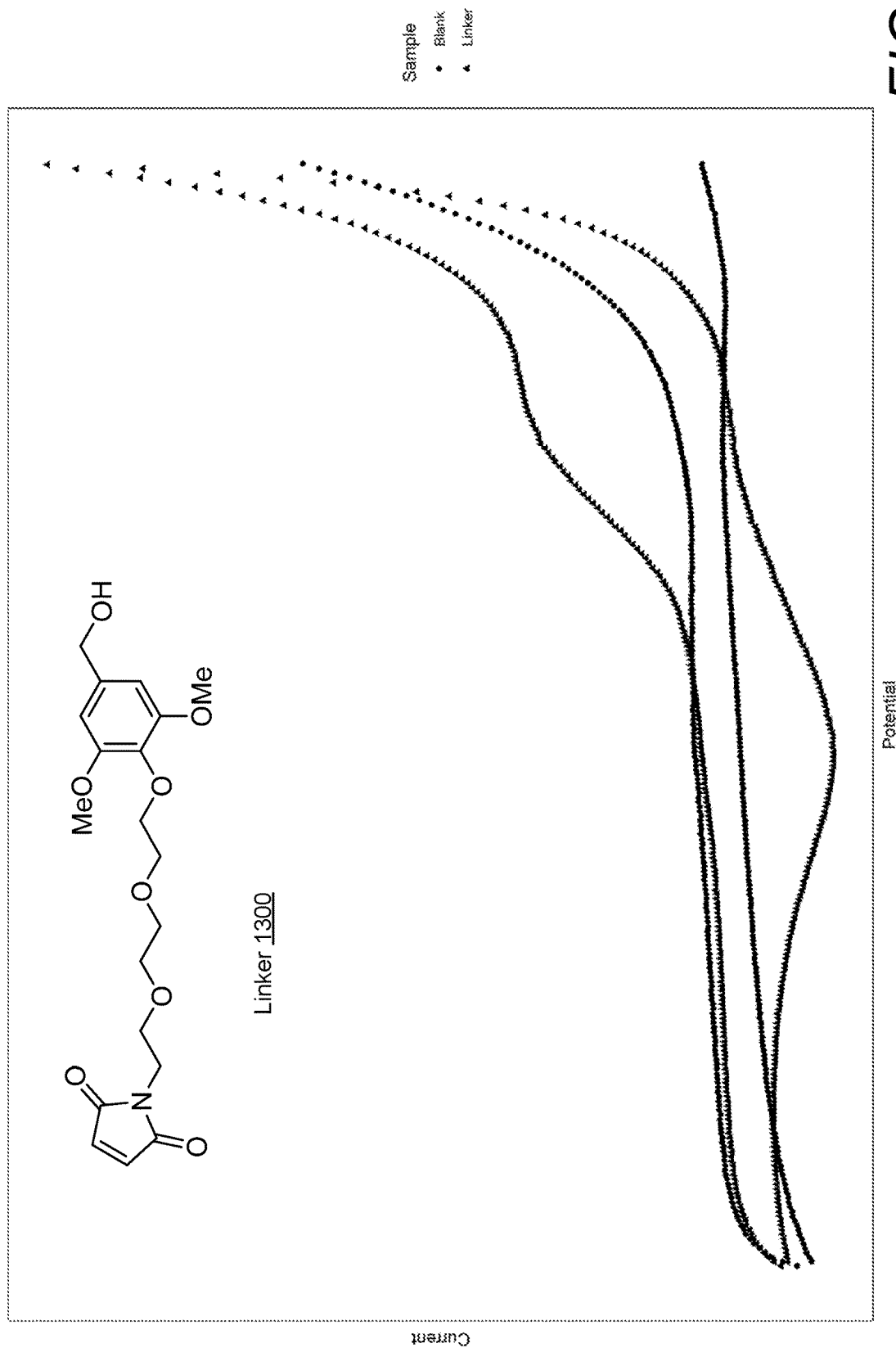
FIG. 13 is a cyclic voltammogram trace showing change in current as the electrode potential is varied in a buffered solution containing a linker with Structure 3 shown in FIG. 5.

FIG. 13 shows a cyclic voltammogram trace for 20 mM of a linker 1300 with a cleavable group that is the same as in Structure 3 shown in FIG. 5 compared to a blank electrochemical cell containing the same solvent. The linker 1300 differs from Structure 3 because it does not include the groups P, $C_2$, $L_2$, $L_3$, or a nucleotide. The electrode potential was generated with a 12.5 mm$^2$ platinum working electrode and a platinum counter electrode using a 10 mV/s sweep rate. The sample containing the linker 1300 exhibits an anodic peak potential at before the asymptotic increase.

Figure 14:
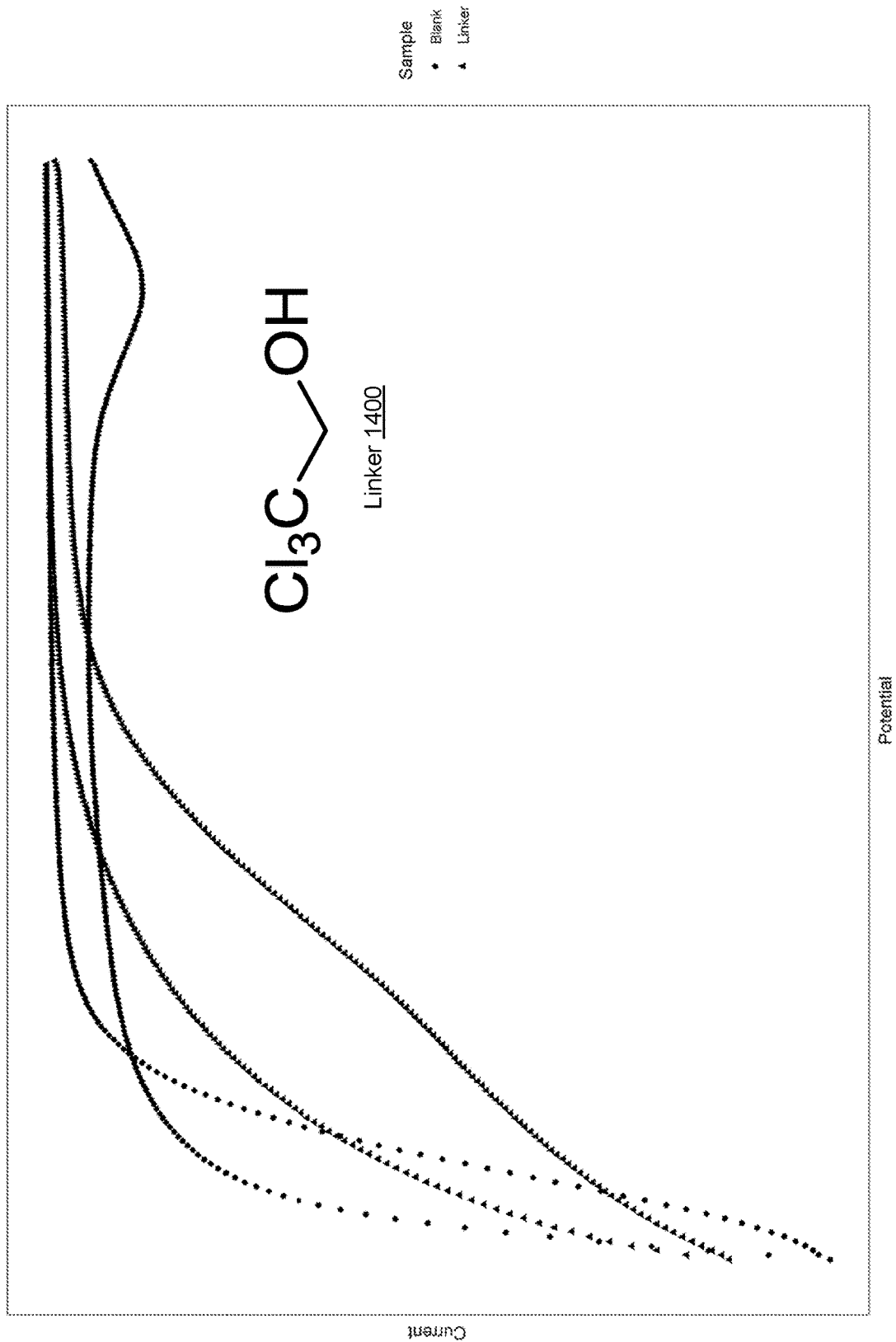
FIG. 14 is a cyclic voltammogram trace showing change in current as the electrode potential is varied in a buffered solution containing a linker with Structure 6 shown in FIG. 8.

FIG. 14 shows a cyclic voltammogram trace measured in μA for 20 mM of a 2,2,2-trichloroethanol linker 1400 that includes the same cleavable group as Structure 6 shown in FIG. 8 compared to a blank electrochemical cell containing the same solvent. The electrode potential was generated with a 20 mm$^2$ carbon working electrode and a carbon counter electrode using a 5 mV/s sweep rate. A subtle reduction peak indicating cleavage of the linker is identifiable as an asymptotic point on the slope of the linker sample. There is not a distinct peak because trichloroethanol reduces through a multi-step reaction that appears as a broad shoulder in the cyclic voltammogram trace.

Figure 15:
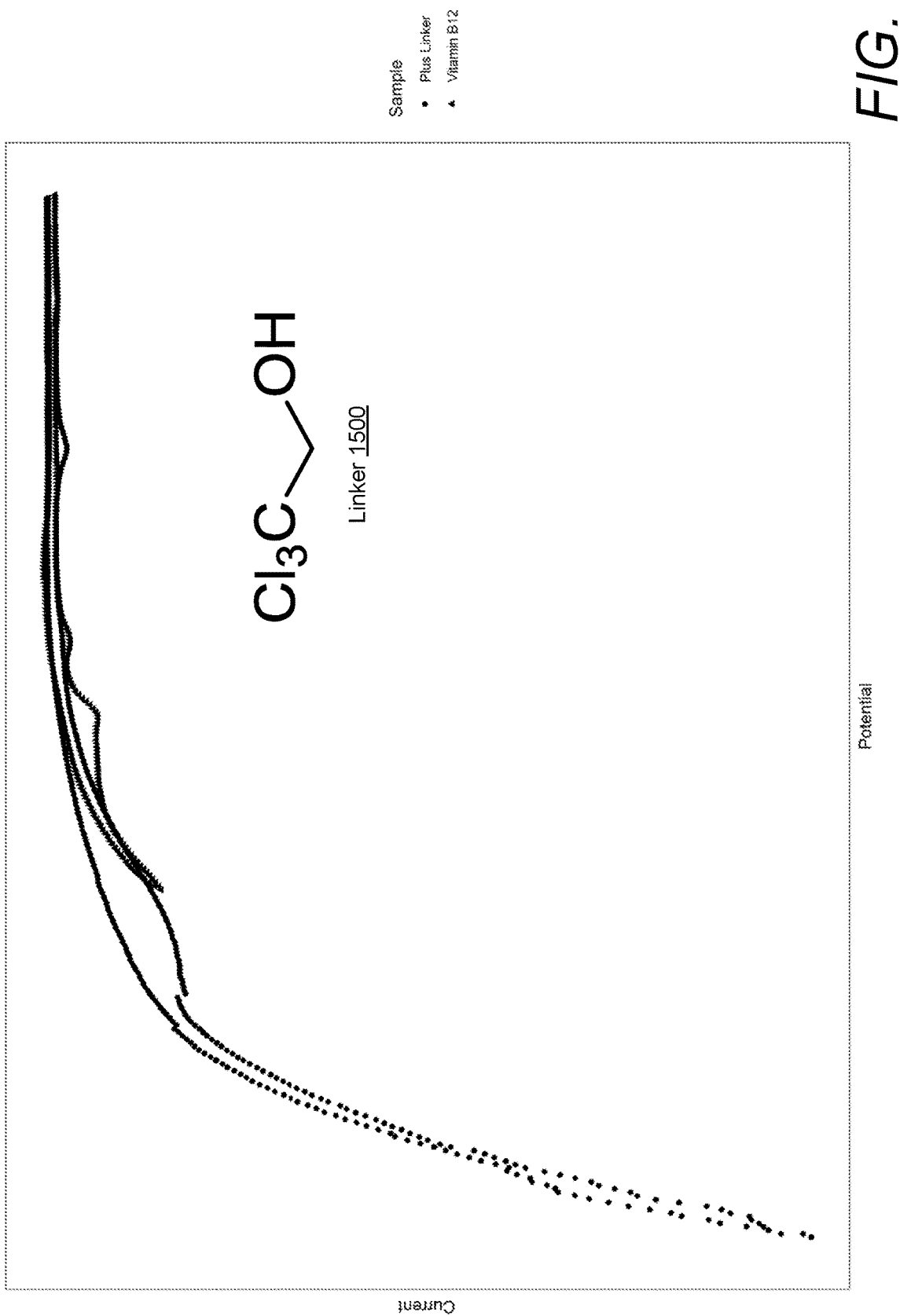
FIG. 15 is a cyclic voltammogram trace showing change in current as the electrode potential is varied in a buffered solution containing a linker with Structure 6 as shown in FIG. 8 in the presence of vitamin $B_{12}$ mediator

FIG. 15 shows a cyclic voltammogram trace for 20 mM 2,2,2-trichloroethanol linker 1500 and 20 mM vitamin $B_{12}$ mediator compared to a blank electrochemical cell containing only the solvent and the vitamin $B_{12}$ mediator. The electrode potential was generated with a 12.5 mm$^2$ platinum working electrode and a platinum counter electrode. The relevant features of the curve are an increase in current and shift in solvent reduction voltage in the sample containing the linker 1500.

Figure 16:
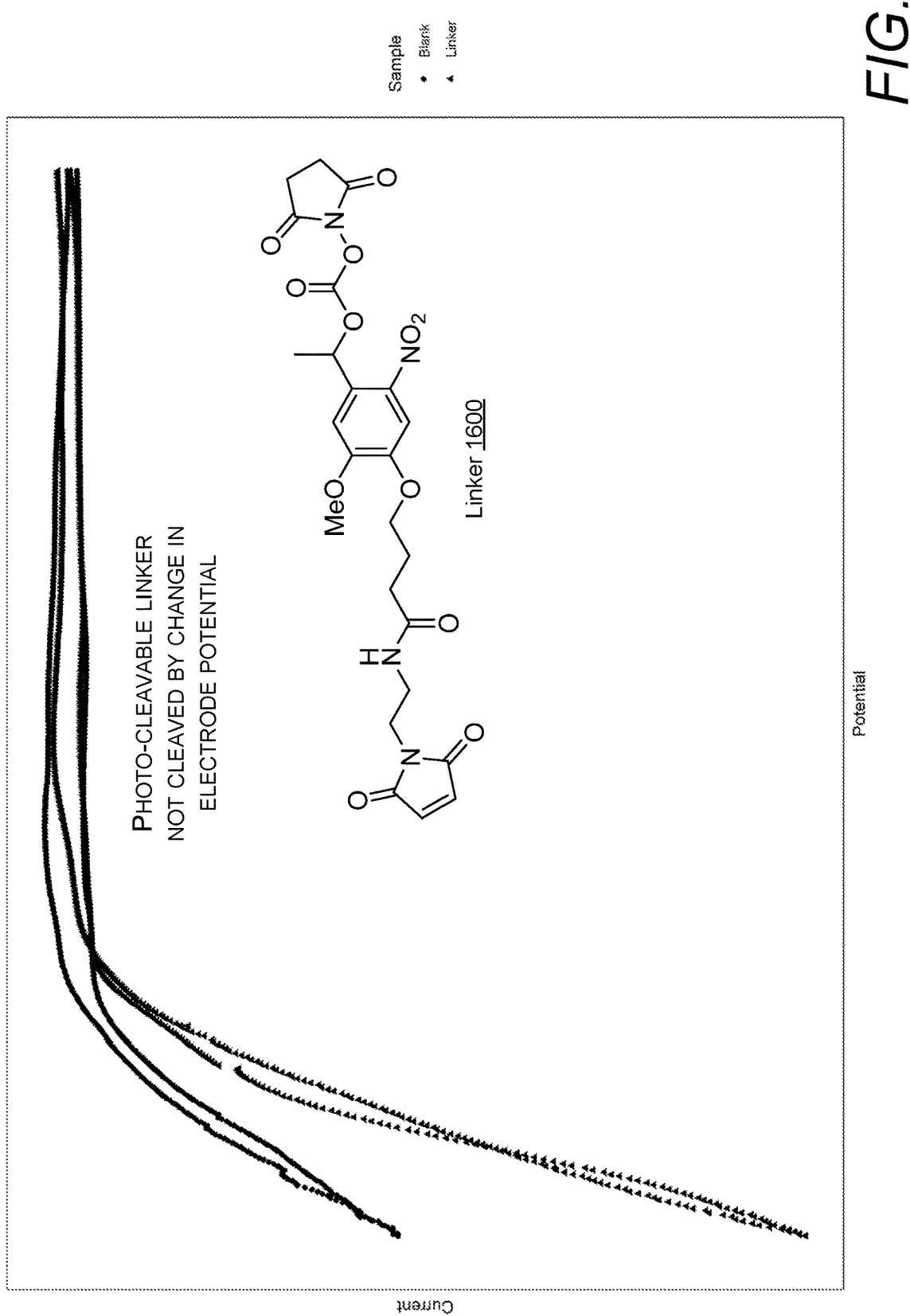
FIG. 16 is a cyclic voltammogram trace showing change in current as the electrode potential is varied in a buffered solution containing a photo-cleavable linker used to attach TdT to a nucleotide for enzymatic nucleotide synthesis.

FIG. 16 shows a cyclic voltammogram trace for 13 mM of the photocleavable linker 1600 from Palluck et al. compared to a blank electrochemical cell containing the same solvent. The electrode potential was generated with a 12.5 mm$^2$ platinum working electrode and a platinum counter electrode using a 100 mV/s sweep rate. The trace does not show a reduction wave prior to the onset of reduction of the blank sample indicating that the linker is not cleaved.

Figure 17:
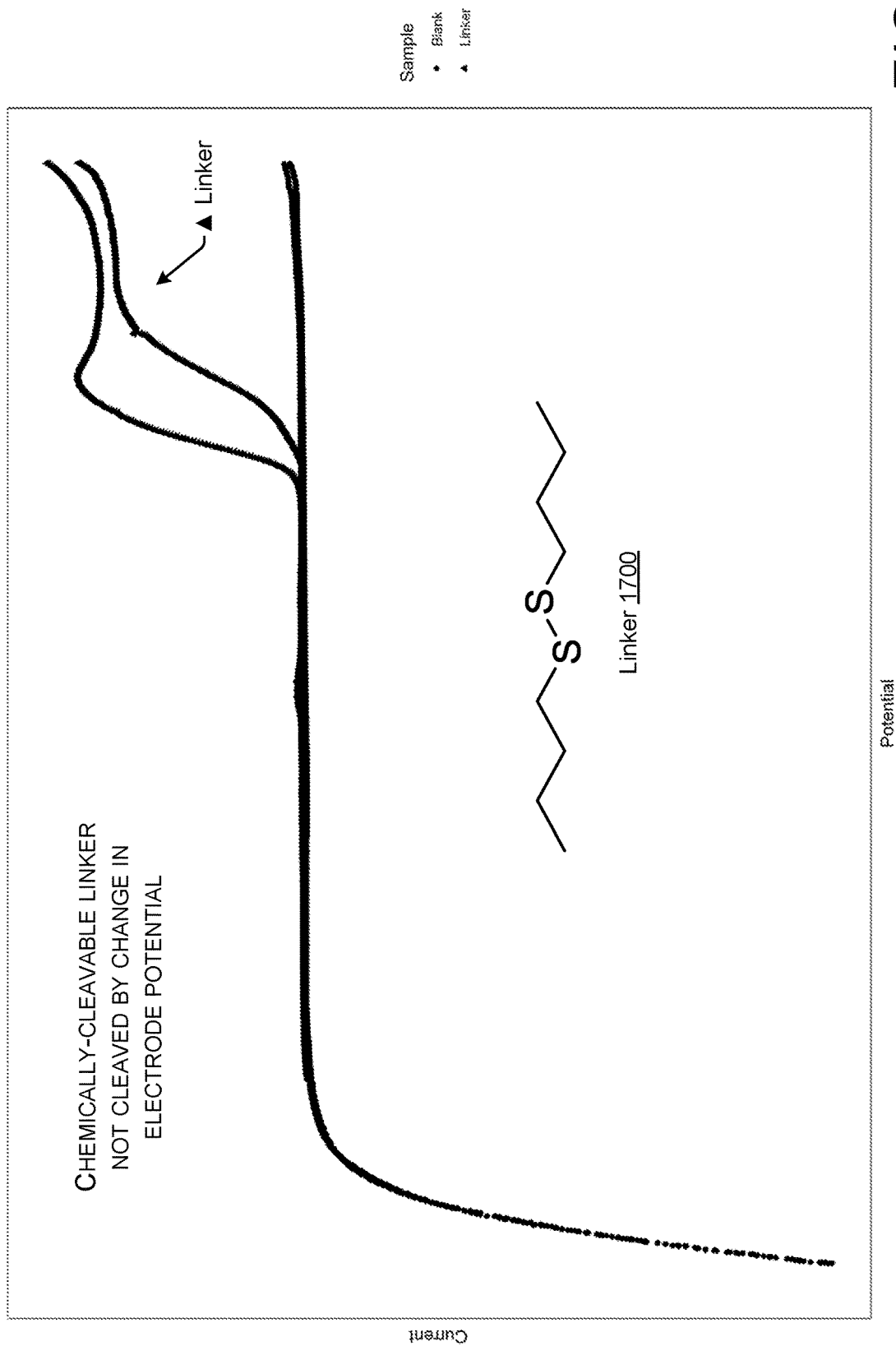
FIG. 17 is a cyclic voltammogram trace showing change in current as the electrode potential is varied in a buffered solution containing a chemically-cleavable linker used to attach TdT to a nucleotide for enzymatic nucleotide synthesis.

FIG. 17 shows a cyclic voltammogram trace for 20 mM of the dibutyl disulfide linker 1700 from Palluck et al. compared to a blank electrochemical cell containing the same solvent. The electrode potential was generated with a 12.5 mm$^2$ platinum working electrode and a platinum counter electrode using a 100 mV/s sweep rate. The trace does not show a reduction wave prior to the onset of solvent reduction indicating that the linker is not cleaved.

Illustrative Linker Synthesis

Figure 18:
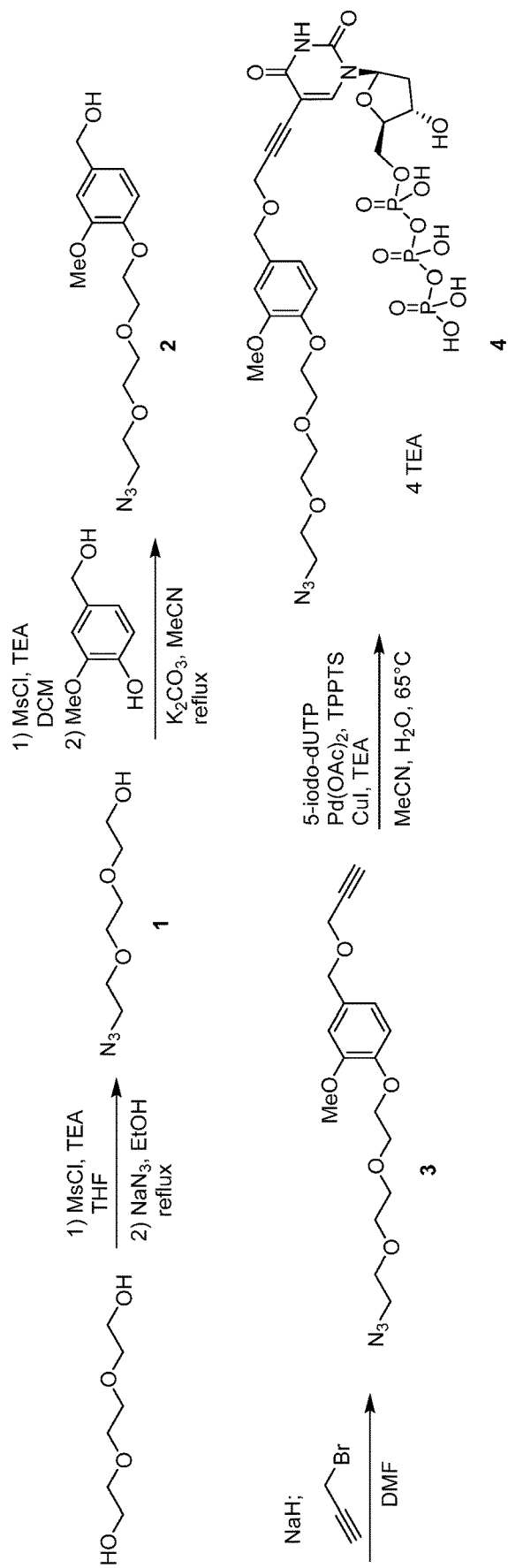
FIG. 18 shows the steps of synthesizing an illustrative electrochemically-cleavable linker.

FIG. 18 shows an example series of four synthetic steps used to make an example linker with the features described in this disclosure. A similar synthetic process may be used to make any of the other linkers provided in this disclosure. Persons of ordinary skill in the art will readily understand how to modify the process described below to generate other linkers such as, for example, linkers with Structure 1, Structure 2, Structure 3, Structure 4, Structure 5, or Structure 6. Examples of suitable techniques may be found in Francis Carey & Robert Giuliano, *Organic Chemistry* (11th ed. 2020) and Peter G. M. Wuts, *Green's Protective Groups in Organic Synthesis* (5th ed. 2014).

Step 1: a) A solution of triethylene glycol (6.64 mL, 2 eq) and triethylamine (16.6 mL, 4.8 eq) in tetrahydrofuran (THF) (50 mL) was cooled in an ice/water bath. A solution of methanesulfonyl chloride (1.93 mL, 1 eq) in THF (8 mL) was added dropwise, and the reaction mixture was allowed to warm to room temperature overnight. The volatiles were removed in vacuo. The residue was suspended in EtOH and concentrated in vacuo.

b) The crude mesylate was dissolved in EtOH (60 mL). Sodium azide (3.25 g, 2 eq) was added, and the resulting suspension was refluxed overnight. The volatiles were removed in vacuo. The residue was diluted with half-saturated brine, washed with three portions of cyclohexane, then extracted with four portions of dichloromethane (DCM). The combined DCM layers were dried over $MgSO_4$ and concentrated in vacuo. The crude material was purified by flash column chromatography on silica gel, eluting with a gradient from 0-8% MeOH in $CDCl_3$ to give 2.16 g pale yellow oil (49%).

Step 2: a) Methanesulfonyl chloride (1.04 mL, 1.1 eq) was added dropwise to a solution of the product generated in step 1 (2.16 g, 1 eq) and triethylamine (5.14 mL, 3 eq) in DCM (45 mL). The resulting suspension was stirred for 1 h. The reaction mixture was diluted with DCM, washed with water, 1 M HCl (aq), and saturated $NaHCO_3$, dried over $Na_2SO_4$, and concentrated in vacuo.

b) The crude mesylate was dissolved in acetonitrile (50 mL). 4-hydroxy-3-methoxybenzyl alcohol (2.28 g, 1.2 eq) and potassium carbonate (2.55 g, 1.5 eq) were added, then the resulting mixture was refluxed overnight. The reaction mixture was cooled to room temperature and filtered, washing with EtOH, and the filtrate concentrated in vacuo. The crude material was purified by flash column chromatography on silica gel, eluting with a gradient from 0-6% MeOH in $CDCl_3$ to give 3.07 g pale yellow, viscous oil (80%). $^1H$ NMR (300 MHz, $CDCl_3$) δ=6.94-6.81 (m, 3H), 4.62 (d, J=5.5 Hz, 2H), 4.18 (dd, J=6.0, 5.0 Hz, 2H), 3.91-3.86 (m, 2H), 3.87 (s, 3H), 3.77-3.72 (m, 2H), 3.70-3.66 (m, 4H), 3.38 (t, J=5.0 Hz, 2H).

Step 3: A solution of the product generated in step 2 (1.0 g, 1 eq) in DMF (16 mL) was cooled in an ice/water bath. Sodium hydride (60 wt % in mineral oil) (0.32 g, 2.5 eq) was added, and the resulting suspension was stirred for 30 min. Propargyl bromide (80 wt % in toluene) was added, and the resulting solution was allowed to warm to room temperature overnight. The reaction mixture was quenched with saturated $NH_4Cl$ (aq), diluted further, and extracted with three portions of DCM. The combined organic layers were dried over $MgSO_4$ and concentrated in vacuo. The crude residue was purified by flash column chromatography, eluting with DCM to provide 0.84 g yellow oil (75%). $^1H$ NMR (300 MHz, $CDCl_3$) δ=6.95-6.84 (m, 3H), 4.54 (s, 2H), 4.22-4.16 (m, 2H), 4.15 (d, J=2.5 Hz, 2H), 3.89 (t, J=5.0 Hz, 2H), 3.86 (s, 3H), 3.77-3.72 (m, 2H), 3.71-3.66 (m, 4H), 3.38 (t, J=5.0 Hz, 2H), 2.47 (t, J=2.5 Hz, 1H).

Step 4: Cuprous iodide (2.4 mg, 0.2 eq) and triethylamine (50.1 μL, 7.2 eq) were added to a degassed solution of 5-iodo-2'-deoxyuridine-5'triphosphate tetratriethylamine salt (50 mg, 1 eq) and the product generated in step 3 (35 mg, 2 eq) in a 2:1 mixture of $H_2O$ and acetonitrile. An independently degassed solution of palladium(II) acetate (1.1 mg, 0.1 eq) and 3,3',3"-phosphanetriyltris(benzenesulfonic acid) trisodium salt (14.2 mg, 0.5 eq) in a 2:1 mixture of $H_2O$ and acetonitrile was added, and the resulting mixture was shaken at 65° C. for 1 h. The reaction mixture was cooled to room temperature and filtered, washing with deionized water. The filtrate was purified by ion exchange chromatography on diethylaminoethyl cellulose (DEAE) Sephadex, eluting with a gradient from 0-1 M TEAB buffer to give the desired product.

Illustrative Embodiments

The following clauses described multiple possible embodiments for implementing the features described in this disclosure. The various embodiments described herein are not limiting nor is every feature from any given embodiment required to be present in another embodiment. Any two or more of the embodiments may be combined together unless context clearly indicates otherwise. As used in this document "or" means and/or. For example, "A or B" means A without B, B without A, or A and B. As used herein, "comprising" means including all listed features and potentially including addition of other features that are not listed. "Consisting essentially of" means including the listed features and those additional features that do not materially affect the basic and novel characteristics of the listed features. "Consisting of" means only the listed features to the exclusion of any feature not listed.

Clause 1. A compound having a structure P—Y-$L_1$-$C_1$-$C_2$-$L_2$-$L_3$-nucleotide, wherein:

P is optionally a bound group that is a peptide, a linked nucleotide, a fluorophore, or a water-soluble group;

Y is optionally a bound group attachment group with the structure:

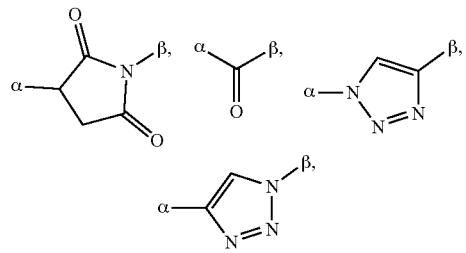

α-S-β, or α-$NH_2$-β, wherein α represents a point of attachment to P and β represents a point of attachment to $L_1$ or $C_1$;

$L_1$ is optionally a flexible extension with the structure:

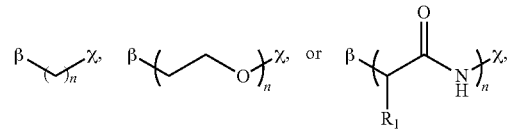

wherein n is 1-20, $R_1$ is hydrogen or a substituted or unsubstituted straight or branched alkyl group having 1 to 6 carbon atoms, wherein b represents a point of attachment to Y or P and c represents a point of attachment to $C_1$;

$C_1$ is a cleavable group with the structure:

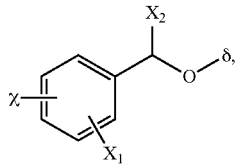

wherein $X_1$ is 1 to 4 ring substituents consisting of a hydrogen, a hydroxyl group, an ether group with an alkyl group having 1 to 3 carbon atoms, an amine group which is unsubstituted or substituted with one or two alkyl groups having 1 to 2 carbon atoms, an alkyl group having 1 to 2 carbon atoms, or a halogen and $X_2$ is hydrogen, a methyl group, an ethyl group, or an isopropyl group,

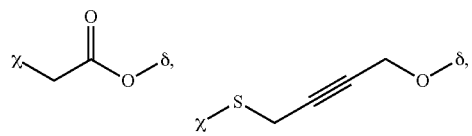

or

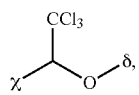

wherein c represents a point of attachment to $L_1$, Y, or P and δ represents a point of attachment to $C_2$, $L_2$, or $L_3$;

$C_2$ is optionally an extension of $C_1$ with the structure:

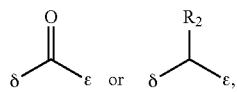

wherein $R_2$ is hydrogen or a substituted or unsubstituted straight or branched alkyl group having 1 to 6 carbon atoms, d represents a point of attachment to $C_1$ and ε represents a point of attachment to $L_2$ or $L_3$;

$L_2$ is optionally flexible extension with the structure:

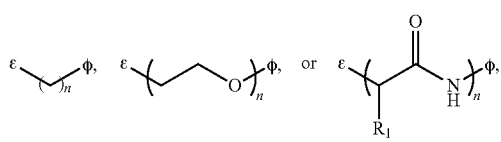

wherein n is 1-20, $R_1$ is hydrogen or a substituted or unsubstituted straight or branched alkyl group having 1 to 6 carbon atoms, wherein & represents a point of attachment to $C_1$ or $C_2$ and φ represents a point of attachment to $L_3$ and wherein at least one of $L_1$ or $L_2$ is present, and $L_3$ is a nucleotide attachment group with the structure:

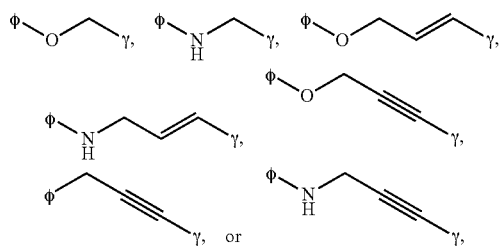

wherein φ represents a point of attachment to $C_1$, $C_2$, or $L_2$ and γ represents a point of attachment to the nucleotide.

Clause 2. The compound of clause 1, wherein P is present, Y is present, L1 is present, C2 is present, L2 is omitted, and L3 is present.

Clause 3. The compound of the compound of any of clauses 1-2, wherein P is present and a peptide, wherein the peptide is an enzyme.

Clause 4. The compound of clause 3, wherein the enzyme is TdT.

Clause 5. The compound of any of clauses 1-2, wherein P is present and a linked nucleotide comprising at least one of DNA, RNA, or a synthetic nucleotide having a universal base.

Clause 6. The compound of any of clauses 1, 2, 5, wherein P is present and a linked nucleotide that is complementary to the nucleotide.

Clause 7. The compound of any of clauses 1-6, wherein Y is present and is

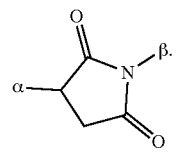

Clause 8. The compound any of clauses 1-7, wherein L2 is omitted.

Clause 9. The compound of any of clauses 1-8, wherein L1 is present and is

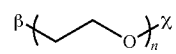

and n is 2.

Clause 10. The compound of any of clauses 1-9, wherein:
$C_1$ is

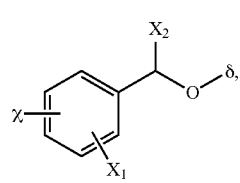

wherein $X_1$ is 1 to 4 ring substituents consisting of a hydrogen, a hydroxyl group, an ether group with an alkyl group having 1 to 3 carbon atoms, an amine group which is unsubstituted or substituted with one or two alkyl groups having 1 to 2 carbon atoms, an alkyl group having 1 to 2 carbon atoms, or a halogen and $X_2$ is hydrogen, a methyl group, an ethyl group, or an isopropyl group; and $C_2$ is

Clause 11. The compound of clause 9, wherein X1 is hydrogen and X2 is hydrogen.

Clause 12. The compound of clause 9, wherein X1 is a methyl ether and X2 is hydrogen.

Clause 13. The compound of any of clauses 1-9, wherein C1 is

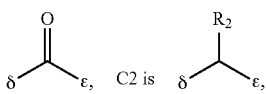

and R2 is hydrogen.

Clause 14. The compound of any of clauses 1-9, wherein C1 is

and C2 is

Clause 15. The compound of any of clauses 1-9, wherein C1 is

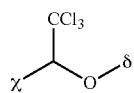

and C2 is

Clause 16. The compound of any of clauses 1-15, wherein L3 is

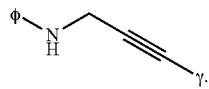

Clause 17. The compound of any of clauses 1-16, wherein the nucleotide comprises a DNA nucleotide triphosphate or an RNA nucleotide triphosphate.

Clause 18. The compound of any of clauses 1-17, wherein the base of the nucleotide is a pyrimidine base and L3 is attached to the number 5 carbon of the pyrimidine base or the base of the nucleotide is a purine base and L3 is attached to the number 7 nitrogen of the purine base.

Clause 19. The compound of claim 1 having the structure:

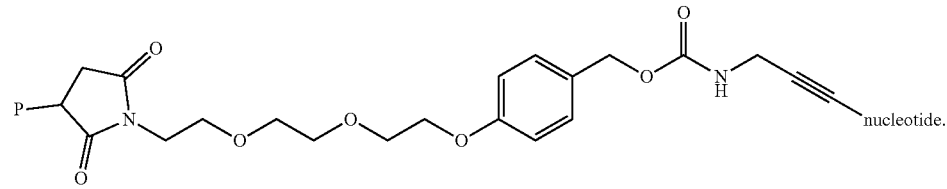

Clause 20. The compound of claim 1 having the structure:

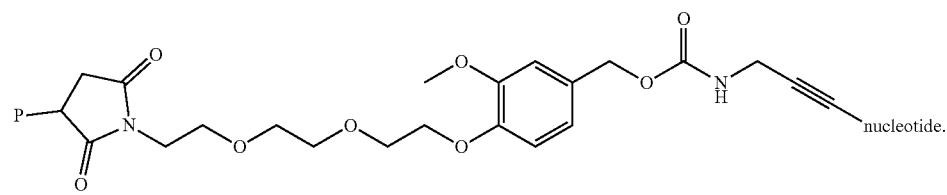

Clause 21. The compound of claim 1 having the structure:

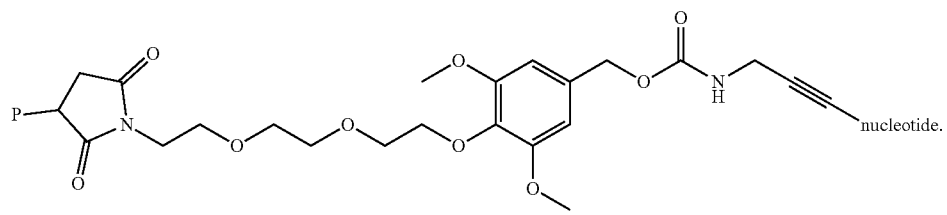

Clause 22. The compound of claim 1 having the structure:

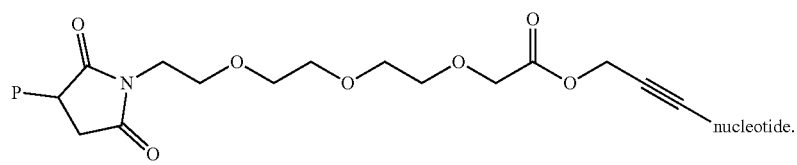

Clause 23. The compound of claim 1 having the structure:

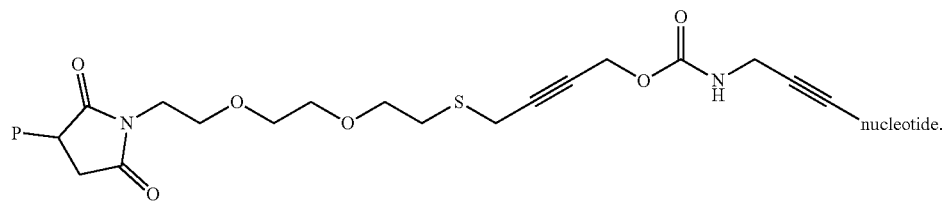

Clause 24. The compound of claim 1 having the structure:

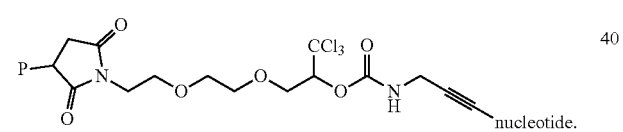

Clause 25. A method of enzymatic oligonucleotide synthesis comprising: selectively creating an electrode potential less than the hydrolysis potential of water at one or more microelectrodes on an electrode array thereby cleaving blocking groups from the ends of growing oligonucleotide strands; and contacting the surface of the electrode array with a predetermined nucleotide attached to a blocking group via a electrochemically-cleavable linker with a cleavage potential less than the hydrolysis potential of water.

Clause 26. The method of clause 25, wherein the electrochemically-cleavable linker is a compound of any of clauses 1-24.

Clause 27. A method of cleaving a linker in a solvent comprising: creating an electrode potential in the solvent that is less than the redox potential of the solvent, wherein the linker has a structure P—Y-L$_1$-C$_1$-C$_2$-L$_2$-L$_3$-nucleotide, wherein:

P is optionally a bound group that is a peptide, a linked nucleotide, a fluorophore, or a water-soluble group;

Y is optionally a bound group attachment group with the structure:

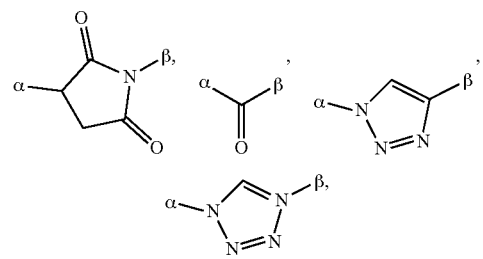

α-S-β, or α-NH$_2$-β, wherein α represents a point of attachment to P and β represents a point of attachment to L$_1$ or C$_1$;

L$_1$ is optionally a flexible extension with the structure:

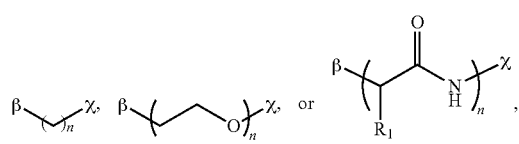

wherein n is 1-20, R$_1$ is hydrogen or a substituted or unsubstituted straight or branched alkyl group having 1 to 6 carbon atoms, wherein β represents a point of attachment to Y or P and χ represents a point of attachment to C$_1$;

$C_1$ is a cleavable group with the structure:

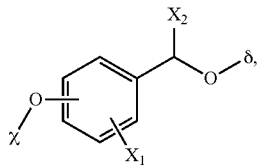

wherein $X_1$ is 1 to 4 ring substituents consisting of a hydrogen, a hydroxyl group, an ether group with an alkyl group having 1 to 3 carbon atoms, an amine group which is unsubstituted or substituted with one or two alkyl groups having 1 to 2 carbon atoms, an alkyl group having 1 to 2 carbon atoms, or a halogen and $X_2$ is hydrogen, a methyl group, an ethyl group, or an isopropyl group,

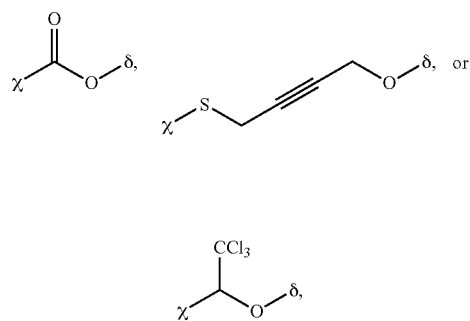

wherein $\chi$ represents a point of attachment to $L_1$, Y, or P and $\delta$ represents a point of attachment to $C_2$, $L_2$, or $L_3$;

$C_2$ is optionally an extension of $C_1$ with the structure:

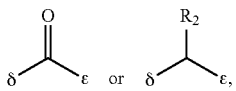

wherein $R_2$ is hydrogen or a substituted or unsubstituted straight or branched alkyl group having 1 to 6 carbon atoms, $\delta$ represents a point of attachment to $C_1$ and $\epsilon$ represents a point of attachment to $L_2$ or $L_3$;

$L_2$ is optionally flexible extension with the structure:

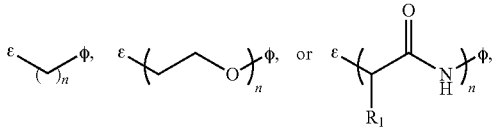

wherein n is 1-20, $R_1$ is hydrogen or a substituted or unsubstituted straight or branched alkyl group having 1 to 6 carbon atoms, wherein ε represents a point of attachment to $C_1$ or $C_2$ and ɸ) represents a point of attachment to $L_3$ and wherein at least one of $L_1$ or $L_2$ is present, and $L_3$ is a nucleotide attachment group with the structure:

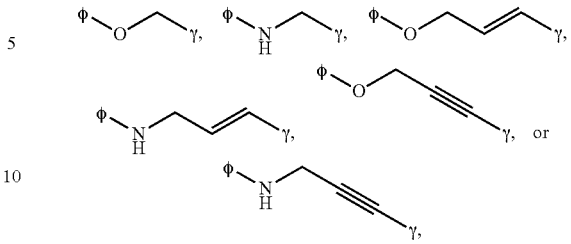

wherein ɸ represents a point of attachment to $C_1$, $C_2$, or $L_2$ and γ represents a point of attachment to the nucleotide.

Clause 28. The method of clause 27, wherein the solvent is an aqueous buffer, an organic solvent, or mixture of an aqueous buffer and organic solvent.

CONCLUSION

Although the subject matter has been described in language specific to structural features and/or methodological acts, it is to be understood that the subject matter defined in the appended claims is not necessarily limited to the specific features or acts described above. Rather, the specific features and acts are disclosed as example forms of implementing the claims.

The terms "a," "an," "the" and similar referents used in the context of describing the invention are to be construed to cover both the singular and the plural unless otherwise indicated herein or clearly contradicted by context. The terms "based on," "based upon," and similar referents are to be construed as meaning "based at least in part" which includes being "based in part" and "based in whole," unless otherwise indicated or clearly contradicted by context. The terms "portion," "part," or similar referents are to be construed as meaning at least a portion or part of the whole including up to the entire noun referenced. As used herein, "approximately" or "about" or similar referents denote a range of ±10% of the stated value.

For ease of understanding, the processes discussed in this disclosure are delineated as separate operations represented as independent blocks. However, these separately delineated operations should not be construed as necessarily order dependent in their performance. The order in which the processes are described is not intended to be construed as a limitation, and unless other otherwise contradicted by context any number of the described process blocks may be combined in any order to implement the process or an alternate process. Moreover, it is also possible that one or more of the provided operations is modified or omitted.

Certain embodiments are described herein, including the best mode known to the inventors for carrying out the invention. Of course, variations on these described embodiments will become apparent to those of ordinary skill in the art upon reading the foregoing description. Skilled artisans will know how to employ such variations as appropriate, and the embodiments disclosed herein may be practiced otherwise than specifically described. Accordingly, all modifications and equivalents of the subject matter recited in the claims appended hereto are included within the scope of this disclosure. Moreover, any combination of the above-described elements in all possible variations thereof is encompassed by the invention unless otherwise indicated herein or otherwise clearly contradicted by context.

Furthermore, references have been made to publications, patents, and/or patent applications throughout this specification. Each of the cited references is individually incorporated herein by reference for its particular cited teachings as well as for all that it discloses.

The invention claimed is:

1. A compound having a structure P—Y-$L_1$-$C_1$-$C_2$-$L_2$-$L_3$-nucleotide, wherein:

P is a bound group that is a peptide, a linked nucleotide, a fluorophore, or a water-soluble group;

Y is optional, if present Y is a bound group attachment group with the structure:

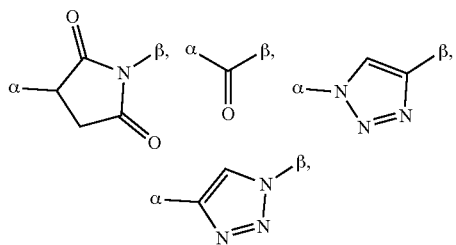

α-S-β, or α-$NH_2$-β, wherein α represents a point of attachment to P and β represents a point of attachment to $L_1$ or $C_1$;

$L_1$ is optional, if present $L_1$ is a flexible extension with the structure one or more of:

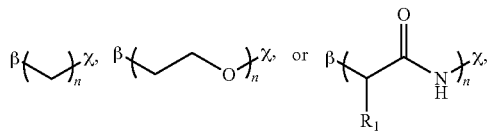

wherein n is 1-20, $R_1$ is hydrogen or a substituted or unsubstituted straight or branched alkyl group having 1 to 6 carbon atoms, wherein β represents a point of attachment to Y or P and χ represents a point of attachment to $C_1$;

$C_1$ is a cleavable group with the structure:

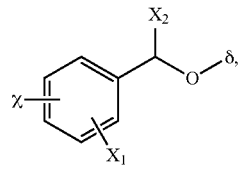

wherein $X_1$ is 1 to 4 ring substituents selected from the group consisting of a hydroxyl group, an ether group with an alkyl group having 1 to 3 carbon atoms, an amine group which is unsubstituted or substituted with one or two alkyl groups having 1 to 2 carbon atoms, an alkyl group having 1 to 2 carbon atoms, and a halogen and $X_2$ is hydrogen, a methyl group, an ethyl group, or an isopropyl group,

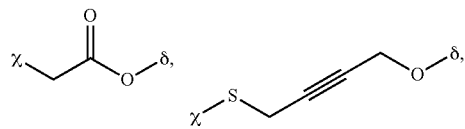

or

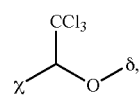

wherein x represents a point of attachment to $L_1$, Y, or P and δ represents a point of attachment to $C_2$;

$C_2$ is an extension of $C_1$ with the structure:

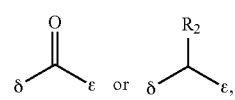

wherein $R_2$ is hydrogen or a substituted or unsubstituted straight or branched alkyl group having 1 to 6 carbon atoms, δ represents a point of attachment to $C_1$ and ε represents a point of attachment to $L_2$ or $L_3$;

$L_2$ is optional, if present $L_2$ is flexible extension with the structure:

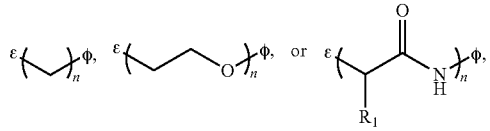

wherein n is 1-20, $R_1$ is hydrogen or a substituted or unsubstituted straight or branched alkyl group having 1 to 6 carbon atoms, wherein ε represents a point of attachment to $C_2$ and φ represents a point of attachment to $L_3$ and wherein at least one of $L_1$ or $L_2$ is present, and $L_3$ is a nucleotide attachment group with the structure:

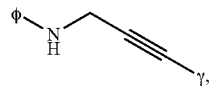

wherein φ represents a point of attachment to $C_1$, $C_2$, or $L_2$ and γ represents a point of attachment to the nucleotide.

2. The compound of claim 1, wherein P is a peptide, wherein the peptide is an enzyme.

3. The compound of claim 2, wherein the enzyme is TdT.

4. The compound of claim 1, wherein P is a linked nucleotide comprising at least one of DNA, RNA, or a synthetic nucleotide having a universal base.

5. The compound of claim 1, wherein P is a linked nucleotide that is complementary to the nucleotide.

6. The compound of claim 1, wherein Y is present and is

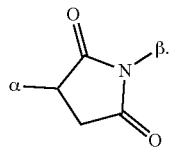

7. The compound of claim 1, wherein:
$C_1$ is

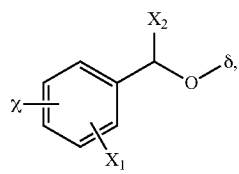

wherein $X_1$ is 1 to 4 ring substituents selected from the group consisting of a hydroxyl group, an ether group with an alkyl group having 1 to 3 carbon atoms, an amine group which is unsubstituted or substituted with one or two alkyl groups having 1 to 2 carbon atoms, an alkyl group having 1 to 2 carbon atoms, and a halogen and $X_2$ is hydrogen, a methyl group, an ethyl group, or an isopropyl group; and

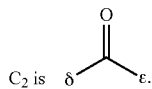

8. The compound of claim 7, wherein $X_2$ is hydrogen.

9. The compound of claim 7, wherein $X_1$ is a methyl ether and $X_2$ is hydrogen.

10. The compound of claim 1, wherein $C_1$ is

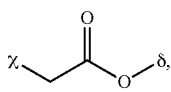

$C_2$ is

and $R_2$ is hydrogen.

11. The compound of claim 1, wherein $C_1$ is

and $C_2$ is

12. The compound of claim 1, wherein $C_1$ is

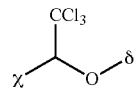

and $C_2$ is

13. The compound of claim 1, wherein the nucleotide comprises a DNA nucleotide triphosphate or an RNA nucleotide triphosphate.

14. The compound of claim 1, wherein the base of the nucleotide is a pyrimidine base and $L_3$ is attached to the number 5 carbon of the pyrimidine base or the base of the nucleotide is a purine base and $L_3$ is attached to the number 7 nitrogen of the purine base.

15. The compound of claim 1, wherein Y is present, $L_1$ is present, $L_2$ is omitted, and $L_3$ is present.

16. The compound of claim 1, wherein $L_2$ is omitted.

17. The compound of claim 16, wherein $L_1$ is present and is

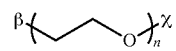

and n is 2 or 3.

18. A compound having a structure P—Y-$L_1$-$C_1$-$C_2$-$L_2$-$L_3$-nucleotide, wherein:
   P is a bound group that is a peptide that is an enzyme, a linked nucleotide comprising at least one of DNA, RNA, or a synthetic nucleotide having a universal base, or a linked nucleotide that is complementary to the nucleotide;
   Y is optional, if present Y is a bound group attachment group with the structure:

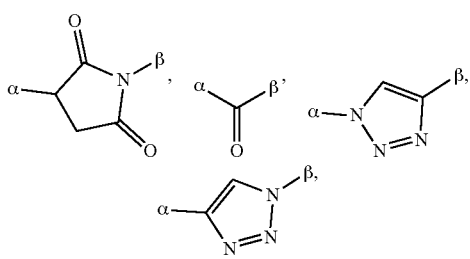

α-S-β, or α-NH$_2$-β, wherein α represents a point of attachment to P and β represents a point of attachment to $L_1$ or $C_1$;

$L_1$ is optional, if present $L_1$ is a flexible extension with the structure one or more of:

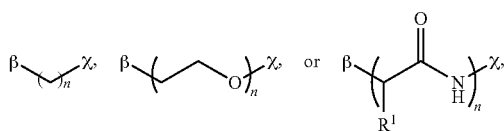

wherein n is 1-20, $R_1$ is hydrogen or a substituted or unsubstituted straight or branched alkyl group having 1 to 6 carbon atoms, wherein β represents a point of attachment to Y or P and χ represents a point of attachment to $C_1$;

$C_1$ is a cleavable group with the structure:

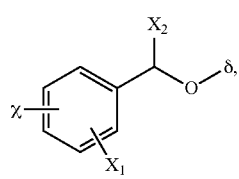

wherein $X_1$ is 1 to 4 ring substituents selected from the group consisting of a hydroxyl group, an ether group with an alkyl group having 1 to 3 carbon atoms, an amine group which is unsubstituted or substituted with one or two alkyl groups having 1 to 2 carbon atoms, an alkyl group having 1 to 2 carbon atoms, and a halogen and $X_2$ is hydrogen, a methyl group, an ethyl group, or an isopropyl group,

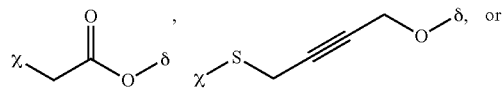

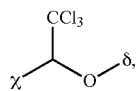

wherein χ represents a point of attachment to $L_1$, Y, or P and δ represents a point of attachment to $C_2$, $L_2$, or $L_3$;

$C_2$ is optional, if present $C_2$ is an extension of $C_1$ with the structure:

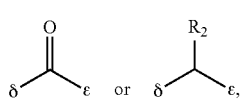

wherein $R_2$ is hydrogen or a substituted or unsubstituted straight or branched alkyl group having 1 to 6 carbon atoms, δ represents a point of attachment to $C_1$ and ε represents a point of attachment to $L_2$ or $L_3$;

$L_2$ is optional, if present $L_2$ is flexible extension with the structure:

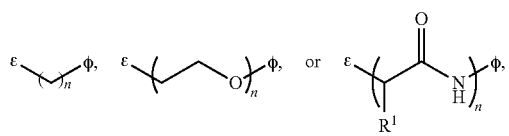

wherein n is 1-20, $R_1$ is hydrogen or a substituted or unsubstituted straight or branched alkyl group having 1 to 6 carbon atoms, wherein ε represents a point of attachment to $C_1$ or $C_2$ and ϕ represents a point of attachment to $L_3$ and wherein at least one of $L_1$ or $L_2$ is present, and $L_3$ is a nucleotide attachment group with the structure:

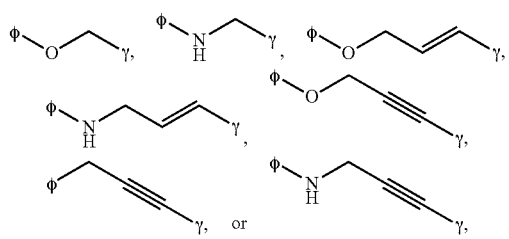

wherein ϕ represents a point of attachment to $C_1$, $C_2$, or $L_2$ and γ represents a point of attachment to the nucleotide.

19. The compound of claim 18, Y is present, $L_1$ is present, $L_2$ is omitted, and $L_3$ is present.

20. A compound having a structure P—Y-$L_1$-$C_1$-$C_2$-$L_2$-$L_3$-nucleotide, wherein:

P is a bound group that is a peptide, a linked nucleotide, a fluorophore, or a water-soluble group;

Y is optional, if present Y is a bound group attachment group with the structure:

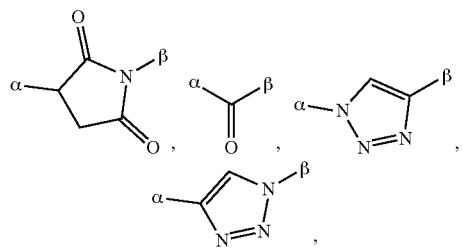

α-S—B, or α-$NH_2$-β, wherein α represents a point of attachment to P and β represents a point of attachment to $L_1$ or $C_1$;

$L_1$ is optional, if present $L_1$ is a flexible extension with the structure one or more of:

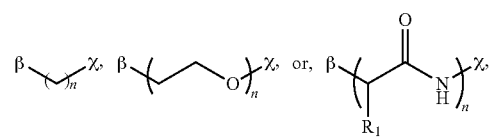

wherein n is 1-20, $R_1$ is hydrogen or a substituted or unsubstituted straight or branched alkyl group having 1 to 6 carbon atoms, wherein β represents a point of attachment to Y or P and χ represents a point of attachment to $C_1$;

$C_1$ is a cleavable group wherein x represents a point of attachment to $L_1$, Y, or P and δ represents a point of attachment to $C_2$, and $C_1$ and $C_2$ have one of the following structures:

$C_1$ is

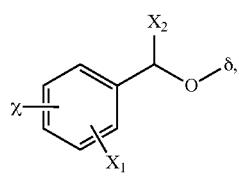

wherein $X_1$ is 1 to 4 ring substituents selected from the group consisting of a hydroxyl group, an ether group with an alkyl group having 1 to 3 carbon atoms, an amine group which is unsubstituted or substituted with one or two alkyl groups having 1 to 2 carbon atoms, an alkyl group having 1 to 2 carbon atoms, and a halogen and $X_2$ is hydrogen, a methyl group, an ethyl group, or an isopropyl group and $C_2$ is

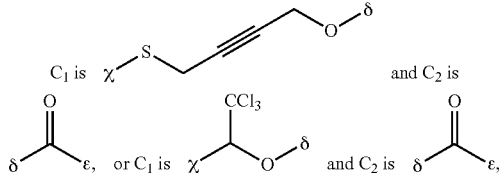

wherein in $C_2$δ represents a point of attachment to $C_1$ and ε represents a point of attachment to $L_2$ or $L_3$;

$L_2$ is optional, if present $L_2$ is flexible extension with the structure:

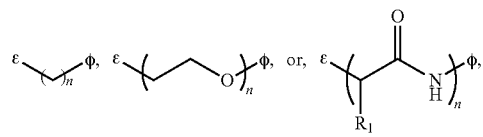

wherein n is 1-20, $R_1$ is hydrogen or a substituted or unsubstituted straight or branched alkyl group having 1 to 6 carbon atoms, wherein ε represents a point of attachment to $C_1$ or $C_2$ and φ represents a point of attachment to $L_3$ and wherein at least one of $L_1$ or $L_2$ is present, and $L_3$ is a nucleotide attachment group with the structure:

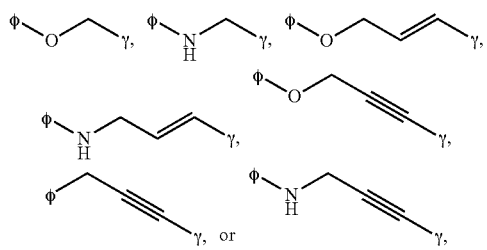

wherein φ represents a point of attachment to $C_2$ or $L_2$ and γ represents a point of attachment to the nucleotide.

21. The compound of claim 20, wherein $C_1$ is

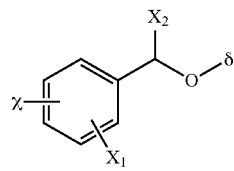

and:
$X_2$ is hydrogen, or
$X_1$ is a methyl ether and $X_2$ is hydrogen.

* * * * *